US012609996B2

(12) United States Patent
Hirst et al.

(10) Patent No.: US 12,609,996 B2
(45) Date of Patent: *Apr. 21, 2026

(54) SELF-DESCRIBING PROTOCOL TRANSLATION DEVICE

(71) Applicant: Drägerwerk AG & Co. KGaA, Lübeck (DE)

(72) Inventors: Michael D. Hirst, Webster, MA (US); Joshua Abell, Beverly, MA (US); John C. Magill, Woburn, MA (US); Andrew T. Provencher, Lowell, MA (US); Brian S. Dolan, Cambridge, MA (US); Justin M. Powell, Danvers, MA (US); Matthew MacDonald, Newburyport, MA (US); Nicholas Comei, Bradford, MA (US); Ellen Benedict, Andover, MA (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/884,719

(22) Filed: Sep. 13, 2024

(65) Prior Publication Data

US 2025/0039274 A1 Jan. 30, 2025

Related U.S. Application Data

(63) Continuation of application No. 17/779,087, filed as application No. PCT/IB2020/000990 on Nov. 25, 2020, now Pat. No. 12,120,196.

(Continued)

(51) Int. Cl.
*H04L 12/24* (2006.01)
*G16H 40/40* (2018.01)
(Continued)

(52) U.S. Cl.
CPC .......... *H04L 67/565* (2022.05); *G16H 40/40* (2018.01); *H04L 67/12* (2013.01); *H04L 69/08* (2013.01)

(58) Field of Classification Search
CPC ....... H04L 67/565; H04L 67/12; H04L 69/08; H04L 67/561; G16H 40/40; G16H 40/60; G16H 10/60
(Continued)

(56) References Cited

U.S. PATENT DOCUMENTS

2008/0197024 A1* 8/2008 Simpson ................ A61B 5/412
204/403.14
2008/0200789 A1* 8/2008 Brister ................ A61B 5/6849
600/347
(Continued)

FOREIGN PATENT DOCUMENTS

EP 3095255 A1 11/2016
WO 2019193211 A1 10/2019

OTHER PUBLICATIONS

International Search Report and The Written Opinion for corresponding International PCT Application No. PCT/IB2020/000990, dated Mar. 16, 2021, 10 pages.
(Continued)

*Primary Examiner* — Moustafa M Meky
*Assistant Examiner* — Elizabeth Kassa
(74) *Attorney, Agent, or Firm* — Nolte Lackenbach Siegel

(57) ABSTRACT

A device and system using same that enables a non-native device to be a self-describing module or communicate in the same protocol as the system protocol for updating data in a medical device and system describing same. In one embodiment, the translation device described herein comprises a processor that converts the non-self-describing protocol (SDP) data into an SDP communication standard and con-
(Continued)

nects to a rack, medical device, a multi-function medical device, or other components within a medical system.

20 Claims, 30 Drawing Sheets

Related U.S. Application Data

(60) Provisional application No. 63/076,210, filed on Sep. 9, 2020, provisional application No. 62/989,196, filed on Mar. 13, 2020, provisional application No. 62/940,669, filed on Nov. 26, 2019.

(51) Int. Cl.

| | | |
|---|---|---|
| *H04L 41/0803* | (2022.01) | |
| *H04L 67/12* | (2022.01) | |
| *H04L 67/565* | (2022.01) | |
| *H04L 69/08* | (2022.01) | |

(58) Field of Classification Search
USPC ........................................................ 709/230
See application file for complete search history.

(56) References Cited

U.S. PATENT DOCUMENTS

| | | | | |
|---|---|---|---|---|
| 2009/0083364 | A1* | 3/2009 | Kitamura | ................ G06F 15/16 |
| | | | | 709/201 |
| 2013/0150692 | A1* | 6/2013 | Kamath | ............... A61B 5/1495 |
| | | | | 600/347 |
| 2014/0140356 | A1* | 5/2014 | Pfutzenreuter | ......... H04L 67/08 |
| | | | | 370/466 |
| 2015/0102681 | A1* | 4/2015 | Leabman | ................ H02J 50/20 |
| | | | | 307/104 |
| 2015/0228186 | A1* | 8/2015 | Jeong | ..................... G08C 17/02 |
| | | | | 340/12.5 |
| 2017/0134536 | A1* | 5/2017 | Tessiore | .................. H04L 69/18 |
| 2017/0163735 | A1* | 6/2017 | Sun | ....................... H04L 67/565 |
| 2017/0169176 | A1* | 6/2017 | Abiola | ................ H04L 63/0428 |
| 2017/0179771 | A1* | 6/2017 | Leabman | ............... H02J 50/30 |
| 2017/0325125 | A1* | 11/2017 | Novo Diaz | ............. H04L 69/04 |
| 2022/0054008 | A1* | 2/2022 | Venkatraman | ......... G16H 50/70 |

OTHER PUBLICATIONS

International Search Report and Written Opinion for corresponding to International PCT Application No. PCT/EP2021/060860, dated Dec. 23, 2021, 11 pages.

Kaspatrtick, Martin et al. "New IEEE 11073 Standards for Interoperable, networked point-of-care Medical Devices" 2015 37th Annual International Conference of the IEEE Engineering in Medicine and Biology Society (EMBC), IEEE, XP032810535, Dated: Aug. 25, 2015, pp. 1721-1724.

China Office Action for corresponding Chinese Application No. 202080094477.4, dated Feb. 26, 2025, 10 pages.

* cited by examiner

500

104

107

2

Network of Medical Computing Devices

Medical Monitoring Device

105

Self-describing Module

1

106

Patient

11

1300

109

53

54

52

55

SDP Translation on
OEM Board in Cable

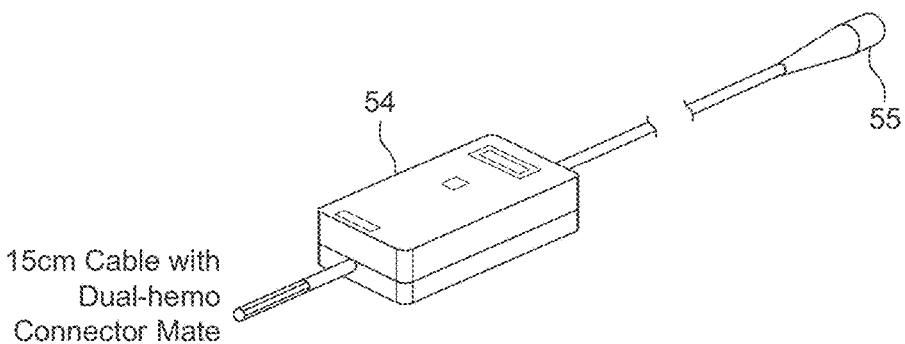

54

55

15cm Cable with
Dual-hemo
Connector Mate

Fig. 20A

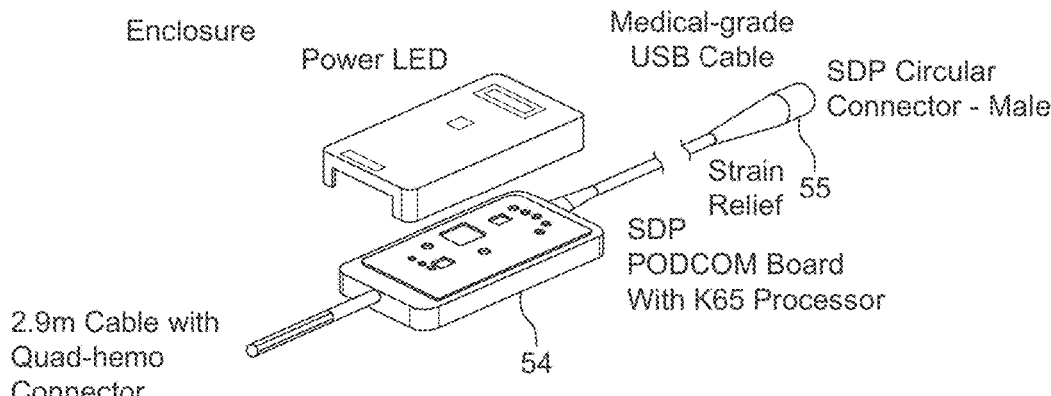

Enclosure

Power LED

Medical-grade
USB Cable

SDP Circular
Connector - Male

Strain
Relief    55

SDP
PODCOM Board
With K65 Processor 2.9m Cable with
Quad-hemo
Connector

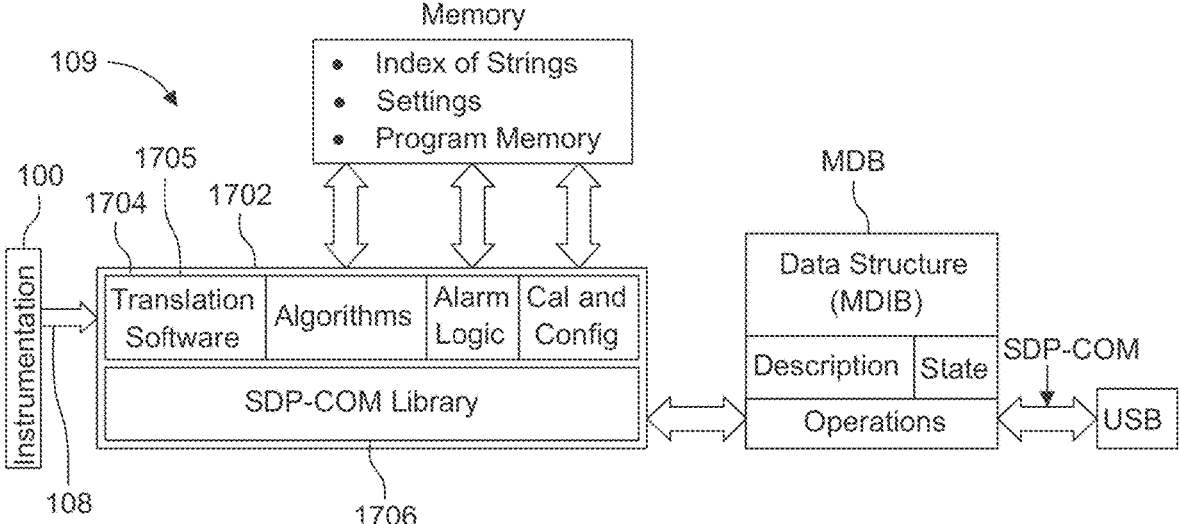

109

1705

1704    1702

100

108

1706

Memory
• Index of Strings
• Settings
• Program Memory

Instrumentation

Translation
Software    Algorithms    Alarm
Logic    Cal and
Config

SDP-COM Library

MDB

Data Structure
(MDIB)

Description    State

Operations

SDP-COM

USB

Fig. 21

SELF-DESCRIBING PROTOCOL TRANSLATION DEVICE

CROSS REFERENCE TO RELATED APPLICATIONS

The present application is a continuation of co-pending U.S. patent application Ser. No. 17/779,087, filed May 23, 2022, which is a nationalization of International Application No. PCT/IB2020/000990, filed Nov. 25, 2020, under 35 U.S.C. § 371, which claimed the priority of U.S. Application Ser. No. 62/940,669, filed Nov. 26, 2019, of U.S. Application Ser. No. 62/989,196, filed Mar. 13, 2020, and of U.S. Application Ser. No. 63/076,210, filed Sep. 9, 2020. Each of the applications International Application No. PCT/IB2020/000990, filed Nov. 25, 2020; U.S. Application Ser. No. 62/940,669, filed Nov. 26, 2019; U.S. Application Ser. No. 62/989,196, filed Mar. 13, 2020; and U.S. Application Ser. No. 63/076,210 are hereby incorporated by reference for all purposes.

FIELD

The subject matter of the present disclosure relates generally to devices for updating data in medical monitoring or therapeutic systems. More specifically, described herein is a device which allows a non-native device or non-self-describing protocol device to operate as an advanced self-describing device and connect to a multi-function medical device

BACKGROUND

Conventional models for interfacing patient physiological sensors to medical devices employ software specifically designed for handling data from a specific sensor and reporting the values to a medical device such as a patient monitor that is programmed to receive and display the data from the specific sensor type. However, these conventional models introduce limitations that need to be addressed. One issue is that it is difficult to add capability to use a new parameter without updating software on the medical device because the medical device must have the specific capability to process the new parameter. Additionally, since both the parameters and software in the medical devices are updated together, they are also tested as a system and released as a system. Moreover, new revisions of the software may not be compatible with previously released medical devices at customer locations. Moreover, a medical device may not be capable of handling data from other sensor device types aside from specific ones it is specifically programmed for or may use a different data/communication protocol than the one used by a particular sensor, thereby limiting its ability to handle or otherwise process data from the sensor device, if at all. Furthermore, a sensor device may not be a self-describing device. Again, this limits the ability of a medical device from handling or otherwise processing data from the sensor device, if at all. Therefore, a device that interfaces between a sensor device and a medical device to ensure the medical device can handle or otherwise process data from the sensor device may be desirable to account for many different types of sensor devices and many different types of data/communication protocols.

SUMMARY

It would be advantageous to provide a device, such as a cable, connector, interface, rack device, or the like, to perform one or more tasks such as communicate, obtain data, describe data, format data, transmit data, or combination(s) thereof to a multi-function medical device, such as a patient monitor, a medical device, a therapy device, or other components in a medical monitoring system from one or more physiological patient parameter sensors or devices that are not self-describing and thus do not use a self-describing protocol (SDP) for data handling and communication. An SDP is a set of rules for communicating and understanding information of limited type using data structures, transmission formats, and defined codes such that a receiver of the information can use, report, or retransmit the information without a priori characterization of the specific received information. It includes any established SDP along with addenda to an established protocol. Thus, a device that is configured with an SDP, including handling, generating, and/or processing data in an SDP format may be referred to herein as a SDP device or a native device, and a non-describing device that is not configured with an SDP for handling, generating, and/or processing data in an SDP format may be referred to herein as a non-SDP (NSDP) device or a nonnative device. Such a non-describing device may be, for example, a physiological patient parameter sensor but is not limited thereto.

These non-SDP devices perform one or more tasks such as communicate, obtain data, describe data, format data, transmit data, or combination(s) thereof in a different communication protocol other than the SDP used by the monitoring system. Thus, it would be advantageous to provide a method to efficiently and easily represent data received from a non-SDP device into an SDP using a structure that allows an SDP device, such as a multi-function medical device, to process this data without a priori information about the data or its source, where process means to analyze, store, present, manipulate, transmit, or any combination thereof.

It would be further advantageous to provide a means to report processed or unprocessed data from a non-SDP device to SDP devices on a communication network that do not have a priori information about the data or its source. Further, it would be advantageous to provide a device, method, or system for a device to describe the information it will transmit to a medical SDP device rather than at least partially relying on a pre-established information or data structure specific to the non-SDP device.

The device, method, and system described herein provides at least one or more of the above advantages by allowing non-SDP devices to perform one or more tasks such as communicate, obtain data, describe data, format data, transmit data, or combination(s) thereof to an SDP device or other system components via the same system protocol as a self-describing device that provides physiological information.

Embodiments described in the present disclosure provide methods, devices, or both for implementing a self-describing module for performing one or more tasks such as communicating data, obtaining data, describing data, formatting data, transmitting data, or combination(s) thereof from a physiological parameter sensor in a medical monitoring system. In one aspect, the methods and devices described herein include a device capable of communication with non-SDP devices via logic, analysis, data formatting, or other means, transmitting a metadata block (MDB) from the self-describing module to the medical device using a communication interface, the MDB including at least identification (ID) data and corresponding configuration data; optionally storing the MDB in memory of the medical device as an instance of MDB data; associating the ID data from the MDB with ID data of a plurality of sub-systems of the medical device; and updating configuration data of al least one sub-system of the medical device with the configuration data in the MDB based on a result of the association between ID data from the MDB and the ID data of sub-systems.

Embodiments described in the present disclosure provide a non-transitory computer-readable recording medium in the self-describing module for updating data in the medical device. The non-transitory computer-readable recording medium stores one or more programs, which when executed by a processor or other means, performs the steps of the method described herein. In one particular embodiment, the non-transitory computer-readable recording medium comprises a translation device that translates the output from the non-SDP device such as a patient sensing device having a first communication protocol to the self-describing communication protocol.

In certain embodiments, the system comprises one or more non-native devices that comprise one or more physiological patient parameters or sensors. In these embodiments, the nonnative devices can communicate to at least one of the self-describing module, the multi-function medical device, the system, or a combination thereof using a translation device such as, without limitation, a translator cable, a translator adaptor, a translator rack, or a translator mount. The translation device comprises a processor that communicates with the non-native devices using the appropriate protocol and then translates the non-SDP device data to the sell-describing communication protocol (i.e., the SDP format). The translation device can be a cable or connector such as, without limitation, a translation cable with a translation board contained therein, or alternatively, a translation device such as a rack or device housing that contains components such as, without limitation, processors, that perform the translation to self-describing protocol from the non-native device. Thus, the translation device translates or otherwise converts data from a non-SDP format into an SDP format so that a multi-function medical device and use or process the data without a priori characterization of the specific received information.

BRIEF DESCRIPTION OF THE DRAWINGS

In the drawings, like reference numbers generally indicate identical, functionally similar, and/or structurally similar elements.

FIG. 11A provides an embodiment of a translation device such as a translation cable, FIG. 11B provides an embodiment of a self-describing module having a double width, FIG. 11C provides an embodiment of a self-describing module having a single width, and FIG. 11D provides an embodiment of a tethered module or pod which does not reside in the mounting rack and is connected to the rack via a cable.

FIGS. 20A and 20B provide an assembled and an exploded diagram, respectively, of an embodiment of the SDP translation cable for hemodynamic sensor devices.

FIG. 21 is a block diagram that shows the functions that the software performs on the translation device.

DETAILED DESCRIPTION

Figure 1:
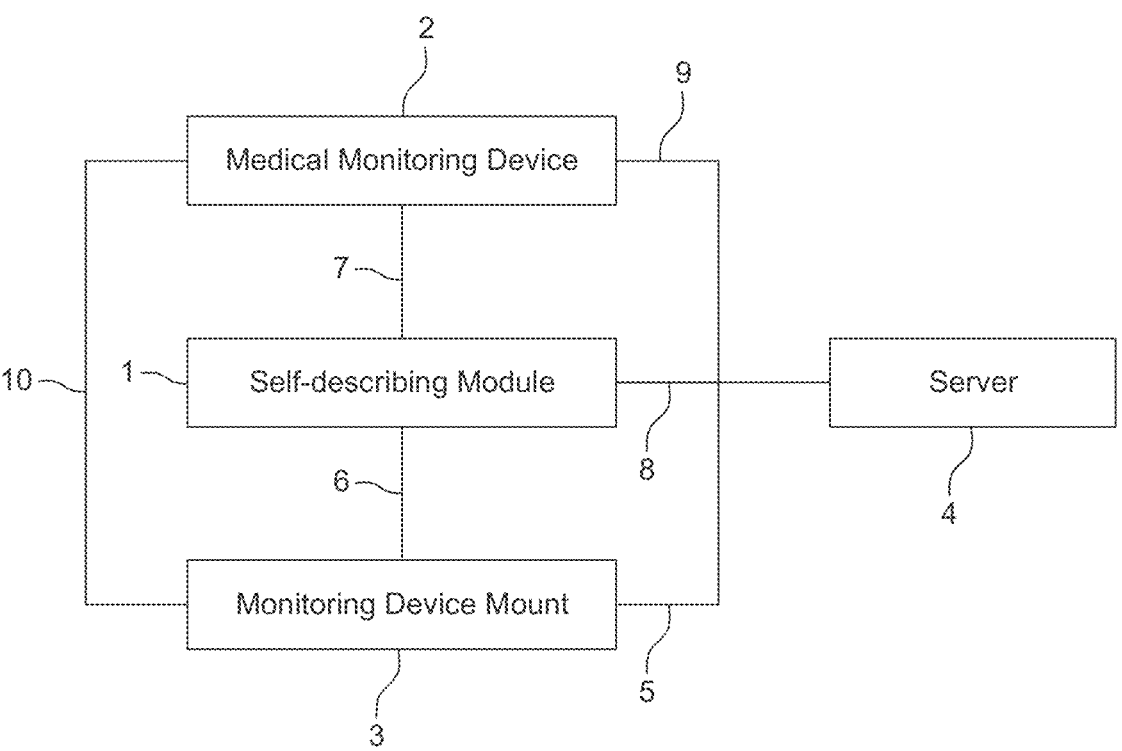
FIG. 1 is a schematic diagram of a system for using a self-describing module for updating data in a medical device according to an embodiment of the present disclosure.

FIG. 1 is a schematic diagram of a system for using a self-describing module for updating data in a medical device. As shown in FIG. 1, the system includes a self-describing module 1, a medical device 2, an optional monitoring device mount 3, and one or more servers 4.

In one particular embodiment, the self-describing module 1, medical device 2, optional monitoring device mount 3, and one or more servers 4 include electronic components or electronic computing devices operable to receive, transmit, process, store, and/or manage data and information associated within a system, which encompasses any suitable processing device adapted to perform computing tasks consistent with the execution of computer-readable instructions stored in a memory or a computer-readable recording medium.

Further, any, all, or some of the computing devices in the self-describing module 1, medical device 2, optional monitoring device mount 3, and one or more servers 4 may be adapted to execute any operating system, including Linux, UNIX, Windows Server, etc., as well as virtual machines adapted to virtualize execution of a particular operating system, including customized and proprietary operating systems. The self-describing module 1, medical device 2, optional monitoring device mount 3, and one or more servers 4 are further equipped with components to facilitate communication with other computing devices over one or more connections 5, 6, 7, 8, 9, and 10. The connections 5, 6, 7, 8, 9, and 10 include connections to local and wide area networks, wireless and wired networks, public and private networks, and any other communication network enabling communication in the system. Additionally, it is also contemplated by the present disclosure that the connections 5, 6, 7, 8, 9, and 10 can include, but are not limited to, a universal serial bus (USB) connection, a serial peripheral interface (SPI) connection, an Ethernet connection, coaxial connection, a wireless connection, a High-Definition Multimedia Interface (HDMI) connection or other serial transport connection, and any combinations thereof.

n FIG. 1, the self-describing module 1, medical device 2, optional monitoring device mount 3, and one or more servers 4 can include one or more programmable data processors and memories or memory locations for storing the software components. In the self-describing module 1, the memory includes a metadata block (MDB). The one or more memories in the self-describing module 1 include, but are not limited to, random access memory (RAM), dynamic random access memory (DRAM), read only memory (ROM), logic blocks of a field programmable gate array (FPGA), erasable programmable read only memory (EPROM), and electrically erasable programmable ROM (EEPROM).

Figure 2:
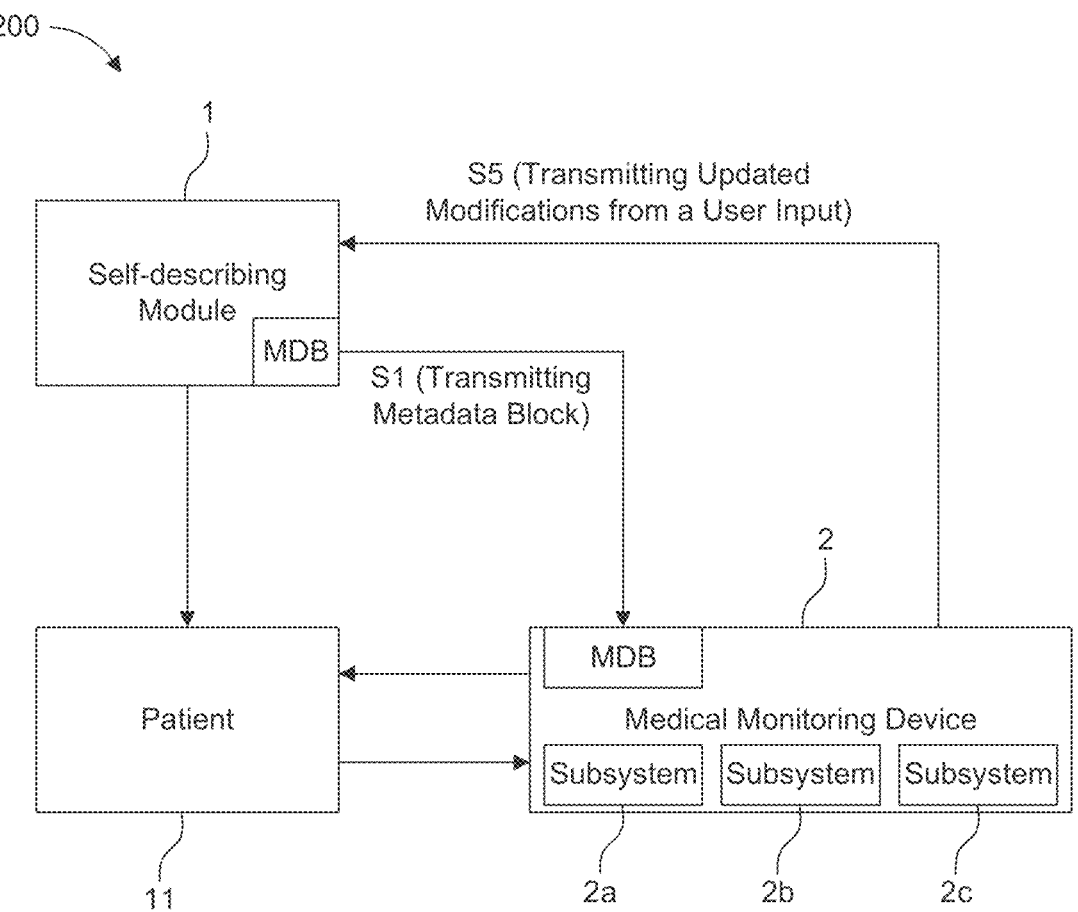
FIG. 2 illustrates a system and a method for using a self-describing module for updating data in a medical device according to one or more embodiments.

Referring to FIG. 2, the self-describing module 1 is a patient monitoring module, or self-describing protocol (SDP) module, configured to acquire and process data generated by at least one physiological sensor configured to monitor a physiological parameter of a patient. The process data generated by sensors such as, without limitation, electrocardiogram (EGG) electrodes, oxygen saturation (Sp02) sensor, blood pressure cuffs, apnea detection sensors, respirators, and others, measure physiological parameters such as blood pressure, heart-related information, pulse oximetry, respiration information, and others.

As noted above, an SDP is a set of rules for communicating and understanding information of limited type using data structures, transmission formats, and defined codes such that a receiver of the information can use, report, or retransmit the information without a priori characterization of the specific received information. It includes any established SDP along with addenda to an established protocol.

The MDB such as that shown in FIG. 2 and the transmission of which is represented in step S1. The MDB includes settings needed by a physiological algorithm of the self-describing module 1. These include patient categories such as neonate, pediatric, or adult. The MDB includes, for example, self-describing module settings of the self-describing module 1 needed by the physiological algorithm such as user changeable filter settings. User changeable filter settings can include values related to limits for alarm settings and other clinical care protocols. The user changeable filter settings are configurable based on patient and may vary from user-to-user (e.g., clinician-to-clinician) and/or patient-to-patient. Having these values in the self-describing module 1 allows for updates and the like to occur through the self-describing module 1 (e.g. updates such as software version revisions, updates, fixes, batches, etc.).

In order to add new functionality or customize, the self-describing module 1 can provide flexibility in several ways. Users can adopt the latest algorithms, features and software updates for parameter measurement devices without waiting for releases of a new version from the medical device 2. Users can configure the number and type of parameter measurement devices to meet varied and changing clinical needs as shown in S5 of FIG. 2. A service approach can be more unified than currently provided, with remote access to versions, logs, self-tests, settings, history, and measurements via the internet or other means to all parameter measurement devices.

The MDB can include data or information for delivering the self-describing configuration of the self-describing module 1 to a consumer such as the medical device 2. The MDB can inform the medical device 2 as to what data is produced as well as additional properties for various sub-systems and display elements within the medical device 2. The MDB can include a plurality of plug-ins, which are software interfaces for allowing communication of the data for the respective subsystems. Each plug-in can engage with the medical device 2. Each plug-in can be implemented for each consumer of the self-describing module 1 data. Additionally, the MDB can include information on how to use the data produced by the self-describing module 1, how data is formatted, how often the data is updated, how the data should be displayed, and how the data should be labelled.

The MDB can include device identification (ID) data such as data types, update rate, alarm limits, settings and other characteristics. Reporting of physiological measurements, for example, and settings including waveforms can be included in the MDB in the form of metrics. Additionally, the MDB supports at least one or more of the following: alerts, remote control of the self-describing module 1, service relevant data retrieval including device meta-data, logs, software updates, and localized text strings with a localized database. The localized text strings include metrics, alerts, and remote control elements supported by the self-describing module 1.

The MDB can also include a subset of data described in a medical device communication standard, which describes and communicates a state of the self-describing module 1. The nomenclature and coding system from the standard, such as IEEE 11073-10207 (Standard for Domain Information and Service Model for Service-Oriented Point-of-Care Medical Device Communication) and 11073-101 (Health informatics—Point-of-care medical device communication—Part 10101: Nomenclature), can provide status of the state of the self-describing module 1. The MDB can include a medical data information base (MDIB), which is a collection of data objects that are provided by a particular medical device including descriptive and state information.

In certain embodiments, the medical device 2 may be a medical monitoring device that is used to monitor various physiological parameters of a patient. A medical monitoring device represents one type of multi-function medical device that uses an SDP to receive and transmit data and is configured to handle or otherwise process data in an SDP format. The medical monitoring device 2 can be portable and travel with the patient in order to provide continuous monitoring during care. The medical monitoring device 2 connects via wired and/or wireless interfaces to one or more sensors such as ECG electrodes, Sp02 sensor, blood pressure cuffs, apnea detection sensors, respirators, and the like which measure the physiological parameters such as blood pressure, heart related information, pulse oximetry, respiration information, and the like associated with the patient. Additional types of information can be conveyed through the medical monitoring device 2. The medical monitoring device 2 can process and/or display analog data derived from the patient.

The medical device 2 includes a plurality of sub-systems. As an example, three different subsystems are shown, including subsystem 2a, subsystem 2b, and subsystem 2c, and each are associated with a unique ID stored at the medical device 2. The plurality of sub-systems can include sub-systems for at least one graphical user interface (GUI), for trends, alarms, reports, networks, and the like. In this or another embodiment, the medical device 2 can include at least one metadata plug-in interface (MPI). Each sub-system of the plurality of sub-systems 2a-2c can include one of the MPIs and each MPI can have a version associated with it. The MPIs engages with the MDB so that plug-ins of the MDB can associate with the MPI of a sub-system. Each of the MPIs can be updated with a new interface while leaving interfaces that are already in place unchanged. The MDB of the self-describing module 1 can include a plurality of plug-ins that connect to the MPIs. The medical device 2 can connect to at least one patient sensor, such as ECG electrodes, Sp02 sensor, blood pressure cuffs, apnea detection sensors, respirators, and the like, that provides patient data to the medical device 2.

The MDB can provide a consumer or user of a medical device 2 with information about what data is being provided and the properties for various sub-systems as well as enable the display of elements within the medical device 2. The MDB includes ID data and corresponding configuration data for the various sub-systems in the medical device 2.

The monitoring device mount 3 can be an optional component. The monitoring device mount 3 can provide physical support, a power source, and a conduit to one or more computer networks. In certain embodiments when the medical device 2 is not used in transport of a patient, the monitoring device mount 3 can be connected. It is contemplated by the present disclosure that, in certain embodiments, the medical device 2 can connect (e.g., connection 6) to the monitoring device mount 3. In these embodiments, the self-describing module 1 connects to the monitoring device mount 3 and communication from the self-describing module 1 to the medical device 2 is established through the monitoring device mount 3 (e.g., connection 10).

Figure 3:
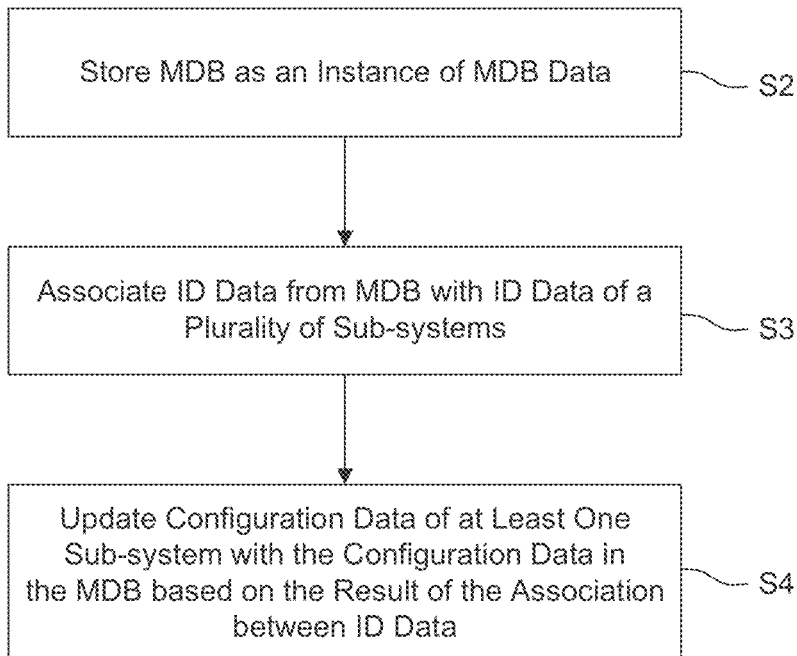
FIG. 3 illustrates a method performed by a medical device for using a self-describing module for updating data in a medical device using the systems in FIGS. 1 and 2 according to one or more embodiments.

FIG. 2 illustrates a system 200 and a method for using a self-describing module 1 for updating data in a medical device 2 according to one or more embodiments. The method is described in conjunction with FIG. 3, which shows additional steps of the method. In step S1, the self-describing module 1 transmits the MDB to the medical device 2. The information provided in the MDB includes the description of metrics that the self-describing module 1 supports. The process performed by the medical device 2 after receiving the MDB is described with reference to FIG. 3 and steps S2-S4. In step S2, the medical device 2 stores the MDB data as an instance of MDB data in the memory of the medical device 2. The instance of MDB data then is used to associate the ID data from the MDB with the ID data of the plurality of sub-systems 2a-2c of the medical device 2 in step S3. When the ID data is unknown to the medical device 2, the ID data can be ignored. In other words, when the ID from the MDB does not match an ID of one of the subsystems 2a-2c, the medical device 2 can ignore the ID data associated with that ID of the MDB. In step S4, updating of configuration data is performed of at least one sub-system of the plurality of sub-systems 2a-2c with the configuration data in the instance of MDB based on the result of the association between the two ID data (i.e., the ID data from the MDB matching the ID data of one of the subsystems 2a-2c). In other words, configuration data associated with an ID of the MDB that matches an ID of a respective subsystem 2a-2c is used to configure, reconfigure, or otherwise update the configuration data of the respective subsystem 2a-2c. At runtime, the state of the metrics change in the MDB and are received by the medical device 2. In certain embodiments, step S2 is not performed, and the medical device 2 transmits the information from the MDB over the network through one or more of the connections 5, 6, 7, 8, 9, and 10 instead of storing the MDB data as an instance in the memory of the medical device 2. Then in the following step S3, MDB data then is used to associate the ID data from the MDB with the ID data of the plurality of sub-systems in step S3.

In certain situations, a user may desire to adjust the data that is provided by the MDB and self-describing module 1. An example of a change made by a user would be the limits for alarms to be adjusted for a particular care unit. The medical device 2 includes a user interface for facilitating communication between the medical device 2 and the user. The user interface allows a user to input changes to the data. Returning to FIG. 2, a user can transmit updated sub-system data modifications made in the medical device 2 to the self-describing module 1 using the user interface, as shown in step S5. The updated sub-system modifications can be, for example, transmitted from the medical device 2 to the self-describing module 1 in reference to the physiological sensors monitoring a patient.

Further descriptions of the self-describing module and its communication with the medical device 2 and/or other components of the system described herein are provided in pending PCT Application Publ. No. WO 2019/193211 entitled Self-Describing Device which is incorporated herein by reference in its entirety.

Communication between the self-describing module 1 and the medical device 2 can occur in a variety of ways. Communication can first be established in between the self-describing module 1 and the medical device 2 through a physical connection (e.g., connection 7 shown in FIG. 1). Examples of the connection includes a USB port, a SPI port, an Ethernet port, or other similar connection. Once connected, the medical device 2 can then detect the self-describing module 1. In certain embodiments, the self-describing module 1 can have a driver associated with the self-describing module 1 that serves as a low-level communication interface. The driver can enable the medical device 2 to detect the self-describing module 1.

Figure 4:
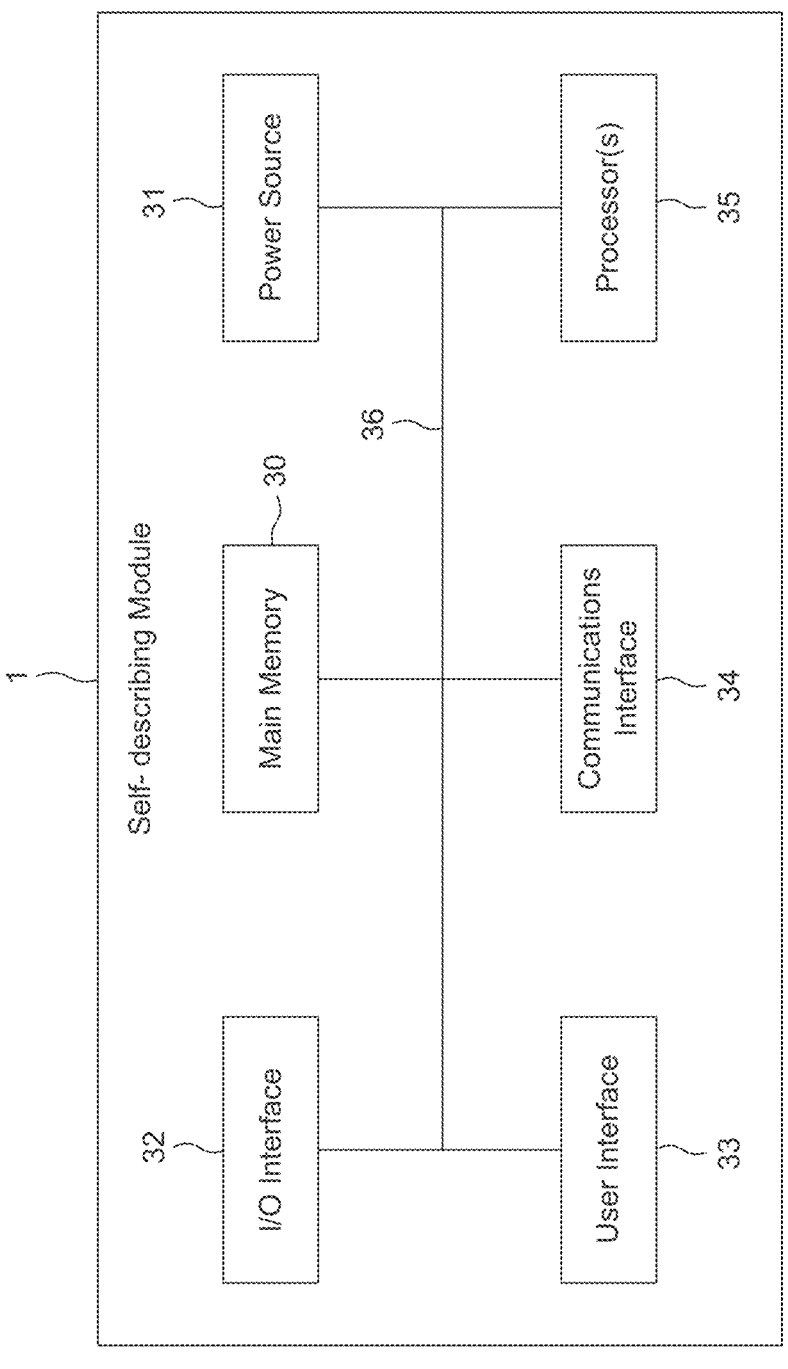
FIG. 4 is a schematic diagram of a self-describing module according to one or more embodiments.

FIG. 4 is a schematic diagram of an example self-describing module 1 according to one or more embodiments. It is contemplated by the present disclosure that the self-describing module 1 includes electronic components or electronic computing devices operable to receive, transmit, process, store, and/or manage data and information associated with the systems and methods previously described, which encompasses any suitable processing device adapted to perform computing tasks consistent with the execution of computer-readable instructions stored in memory or computer-readable recording medium.

Referring to FIG. 4, the example self-describing module 1 includes one or memories or memory locations including a main memory 30 as well as an I/O interface 32, a user interface 33, a communications interface 34, one or more processors 35, and an optional power source 31. The main memory 30 can be a random access memory (RAM), a memory buffer, a hard drive, a database, an erasable programmable read only memory (EPROM), an electrically erasable programmable read only memory (EEPROM), a read only memory (ROM), a flash memory, hard disk or any other various layers of memory hierarchy.

The main memory 30 can be used to store any type of instructions associated with algorithms, processes, or operations for controlling the general functions of the self-describing module 1 including the operations of the MDB as well as any operating system such as Linux, UNIX, Windows Server, or other customized and proprietary operating systems.

The optional power source 31 can be used to power the various components of the self-describing module 1. The power source 31 can be self-contained, such as a battery pack, and/or the power source 31 can include an interface to be powered through an electrical outlet (either directly or by way of the medical device 2 and/or the monitoring device mount 3). In certain embodiments, the self-describing module 1 can only be powered and render information when secured or otherwise connected to one or more of the medical device 2 and the monitoring device mount 3.

The I/O interface 32 can be an interface for enabling the transfer of information between the self-describing module 1 and the external devices such as the medical device 2 or the optional monitoring device mount 3 that need special communication links for interfacing with the one or more processors 35. The I/O interface 32 can be implemented to accommodate various connections to the self-describing module 1 that include, but is not limited to, a USB connection, an SPI connection, an Ethernet connection, coaxial connection, a wireless connection, an HDMI connection or other serial transport connection or other known connection in the art for connecting to external devices.

The user interface 33 is implemented for allowing communication between a user and the self-describing module 1. The user interface 33 includes, but is not limited to, a liquid crystal display (LCD), cathode ray tube (CRT), thin film transistor (TFT), light-emitting diode (LED), high definition (HD) or other similar display device with touch screen capabilities. Other kinds of input devices can be used to provide for interaction with a user as well. For example, feedback provided to the user can be any form of sensory feedback (e.g. visual feedback, auditory feedback by way of a speaker, or tactile feedback), and input from the user can be received in any form, including acoustic, speech, or tactile input. Input devices and a microphone can be coupled to and convey information via the internal bus 36 by way of an input device interface. A speaker can be coupled to and receive information via the internal bus 36 by way of a speaker interface. The self-describing module 1 can omit or one or more of the display, display interface, input device, microphone, speaker, input device interface, and speaker interface. The communications interface 34 is a software and/or hardware interface implemented to establish a connection between the self-describing module 1 and the server 4 in the system described in FIG. 1. It is contemplated by the present disclosure that the communications interface 34 includes software and/or hardware interface circuitry for establishing communication connections with the rest of the system using both wired and wireless connections for establishing connections to, for example, a local area networks (LANs), wide area networks (WANs), metropolitan area networks (MANs) personal area networks (PANs), wireless local area networks (WLANs), system area networks (SANs), and combinations thereof.

The one or more processors 35 are used for controlling the general operations of the self-describing module 1. Each one or the one or more processors 35 can be, but are not limited to, a central processing unit (CPU), a hardware microprocessor, a multi-core processor, a single core processor, a field programmable gate array (FPGA), an application specific integrated circuit (ASIC), a digital signal processor (DSP), or other similar processing device capable of executing any type of instructions, algorithms, or software for controlling the operation of the self-describing module 1. Communication between the components of the self-describing module 1 (e.g., components 30-35) are established using an internal bus 36.

Figure 5:
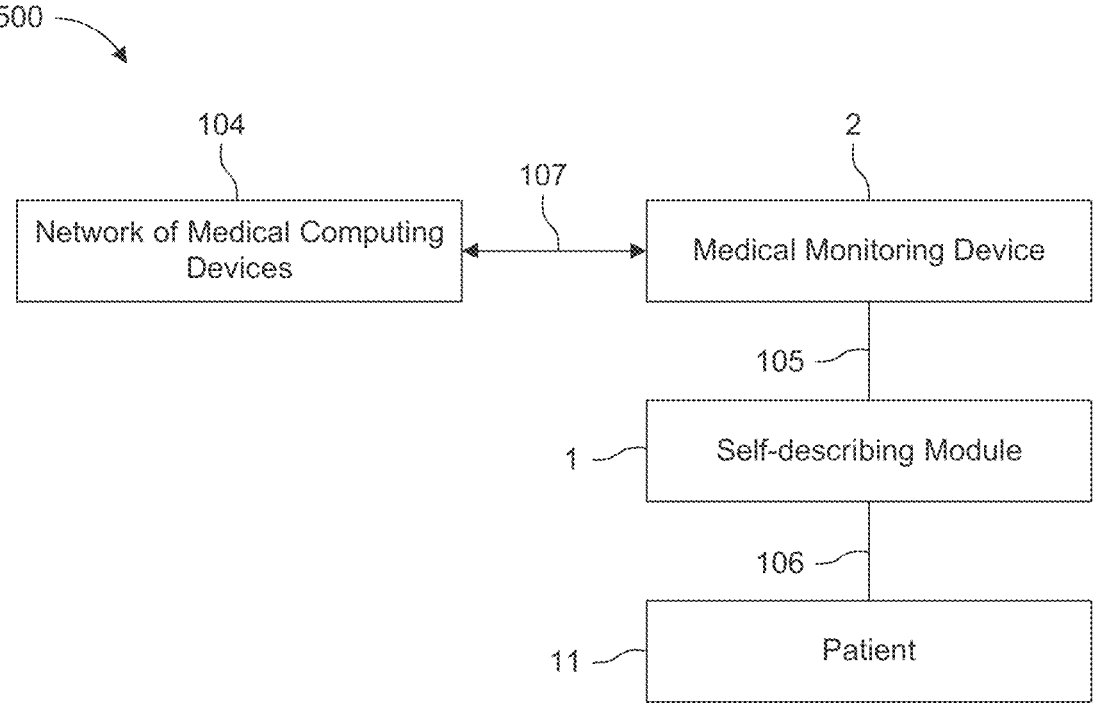
FIG. 5 is a schematic diagram of a system that includes a self-describing module for providing parameter data from a patient to a medical device and further to one or more system components such as a network of medical computing devices according to one or more embodiments.

FIG. 5 is a schematic diagram of an example medical system 500 according to one or more embodiments. It is contemplated by the present disclosure that the medical device 2 includes electronic components or electronic computing devices operable to receive, transmit, process, store, and/or manage data and information associated with the systems and methods previously described, which encompasses any suitable processing device adapted to perform computing tasks consistent with the execution of computer-readable instructions stored in memory or computer-readable recording medium. The medical device 2 is in electrical communication via connection 105 to the self-describing module 1 which is in electrical communication with patient 11 via connection 106. Medical device 2 is in electrical communication via connection 107 to a network of medical computing devices which are shown as 104.

In FIG. 5, the self-describing module 1, medical device 2, network of medical computing devices 104 and the patient 11 comprises components to facilitate communication with other computing devices over one or more connections 105, 106, and 107 (e.g., electrical communication). Connections 105, 106, and 107 include connections to local and wide area networks, wireless and wired networks, public and private networks, and any other communication network enabling communication in the system. Additionally, it is also contemplated by the present disclosure that the connections 105, 106, and 107 can include, but are not limited to, a USB connection, an SPI connection, an Ethernet connection, a coaxial connection, a wireless connection, an HDMI connection or other serial transport connection, and any combinations thereof.

Figure 6:
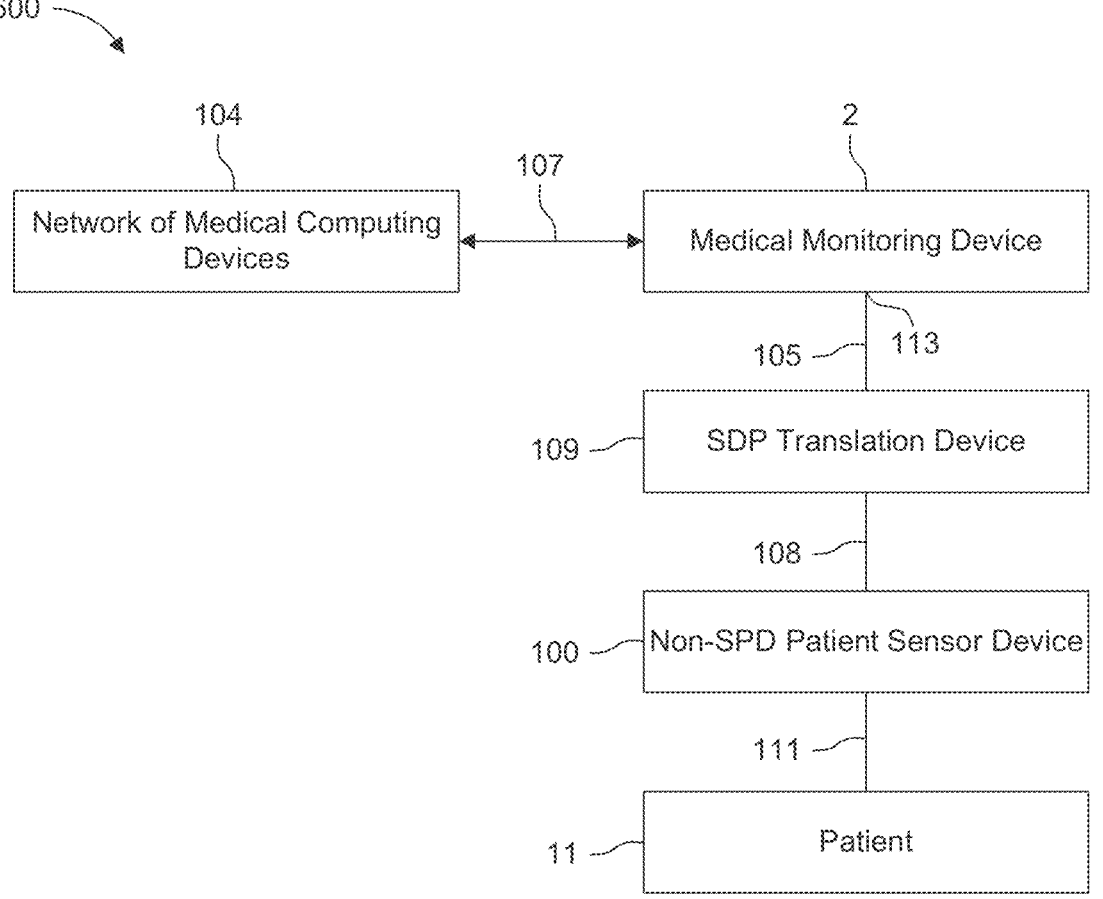
FIG. 6 illustrates a schematic block diagram of a system according to one or more embodiments, wherein a self-describing protocol (SDP) translation device, such as an SDP translation cable, communicates data between a non-SDP device such as a non-native patient sensor device and an SDP medical device and other SDP system components.

FIG. 6 is a schematic block diagram of a medical system 600 according to one or more embodiments. The system 600 includes a non-SDP (NSDP) device (i.e., a non-native device), such as non-SDP (NSDP) patient sensor device 100 which speaks a different communication protocol (e.g., a non-SDP communication protocol or NSDPCOM) than the medical device 2 and the network of medical computing devices 104 or a different system protocol. Said differently, the medical device 2 and the network of medical computing devices 104 are configured to handle or otherwise process data according to an SDP communication protocol (SDPCOM), whereas the non-SDP patient sensor device 100 is not configured to handle or otherwise process data according to the SDP communication protocol. The medical device 2, being an SDP processing device, is unable to process non-SDP (NSDP) data or may only be capable of processing a portion of the non-SDP data due to the mismatch in data protocols.

The system 600 further includes an SDP translation device 109 (i.e., an SDP translator) communicatively coupled between the medical device 2 (i.e., an SDP device) and the non-SDP patient sensor device 100. Thus, the SDP translation device 109 service as an interface between a non-SDP device and an SDP device so that the SDP device can use data generated by the non-SDP device as well as other data (e.g., addenda data, enhanced data, and the like) generated by the SDP translation device 109 without a priori characterization of the specific received information. The data generated by the non-SDP device may include sensor data generated by one or more sensors connected to the patient 11 that measures one or more physiological parameters of the patient 11.

The medical device 2 and the network of medical computing devices 104 may use the SDP for communication, and thus may form an SDP communication network. The SDP is a system protocol used by the network of medical computing devices 104, the medical device 2, and native patient sensor devices, such as the self-describing module 1.

As previously explained, a non-SDP device (i.e., a non-native device), such as the non-SDP patient sensor device 100, is a device that does not use the SDP format its data or for data communications. Instead, the non-SDP device uses a protocol different from the SDP for its data format and its data communications. These non-SDP devices perform one or more tasks such as communicate, obtain data, describe data, format data, transmit data, or combination(s) thereof in a different protocol than the SDP (i.e., the SDP system protocol). As a result, devices, such as the medical device 2, that use the SDP for its data format and communications cannot properly receive, process, and/or display data received from the non-SDP device.

The SDP translation device 109 comprises at least one processor that is configured to translate or otherwise convert the non-SDP data received from the non-SDP patient sensor device 100 into the SDP format and transmits the SDP formatted data to the medical device 2 according to the SDP communications protocol. The medical device 2 is just one example of a multi-function medical device that is used for receiving sensor data from the non-SDP patient sensor device 100.

Because the non-SDP patient sensor device 100 does not communicate with at least one of the medical device 2 or the network of medical computing devices 104 using the SDP (i.e., the SDPCOM), a translation device such as the SDP translation device 109 is used to translate data from the non-native patient sensor device 100, formatted in a non-SDP communication protocol (NSDPCOM), into a data format in the SDP communication protocol (SDPCOM).

As similarly described in reference to FIG. 5, the medical device 2 includes electronic components or electronic computing devices operable to receive, transmit, process, store, and/or manage data and information associated with the systems and methods previously described, which encompasses any suitable processing device adapted to perform computing tasks consistent with the execution of computer-readable instructions stored in memory or computer-readable recording medium. The medical device 2, the SDP translation device 109, the non-native patient sensor device 100, the network of medical computing devices 104, and the patient 11 comprise one or more connections 105, 106, 107, 108, and 111 to facilitate communication between one or more network or system components.

A self-describing module 1 communicates with the medical device 2 and other devices and components within the system (e.g., the network of medical computing devices 104) using the SDP. In certain embodiments, however, the system described herein includes one or more non-SDP physiological patient parameters sensors or devices that do not speak the same SDP communication protocol as the self-describing module 1, the medical device 2, the network of medical computing devices 104, or all of the above within the systems disclosed herein.

For these embodiments, an SDP translation device 109, such as without limitation an SDP translation cable or module, allows the health care provider to use non-SDP, non-native, or OEM devices within the system to communicate with the medical device 2 or other components within the system (e.g., one or more of the medical computing devices or the network of medical computing devices 104).

For these embodiments, a translator cable, a translator connector, a translator interface, a translator module, a translator processor, a translator microcontroller, or the like, each of which is referred to herein as a translation device is used between the non-SDP devices and an input node 113 of the SDP system to allow the non-SDP devices in the system to perform in a similar fashion and communicate via the same protocol or SDP as the self-describing module(s). In this example, the input node 113 of the SDP system is located at an input of the medical device 2 but is not limited thereto. The input node 113 is located at an initial point of contact with the SDP communication network. It is the entry point to the SDP communication network so that all SDP devices can use the SDP formatted data what has been translated, converted, or otherwise reformatted by the SDP translation device 109.

In certain embodiments, the software operating on the processor within the SDP translation device 109 performs one or more of the following functions: translation of data from the non-SDP patient sensor device 100 to a form that can be put in the MDIB of the MDB; calibration process, logic for an alarm condition (e.g., identification of alarm states); user interaction (UI) such as settings menus and alarm limits; algorithms for data analysis; and/or choosing strings from an index, with details described with respect to FIGS. 6 and 7A-7D.

In these or other embodiments, the SDP translation device 109 may further comprise electrical isolation features depending upon the design of the sensing device connected to the patient.

The SDP translation device 109 is configured to allow health care providers who have non-SDP communicating devices to connect them to an SDP-communicating medical device, system, or network. In one embodiment, the SDP translation device 109 allows older versions of products (e.g., sensor devices for physiological parameter detections) which speak in a non-SDP communication protocol to communicate with newer versions of medical devices (e.g., patient monitoring devices and therapy devices), systems, or networks which do speak in a SDP communication protocol. In another embodiment, the SDP translation device 109 allows OEM devices, which speak in a non-SDP communication protocol (NSDPCOM), to communicate with medical devices, systems, or networks which speak in an SDP communication protocol (SDPCOM). As such, users are enabled to easily accommodate existing products (e.g., sensor devices) or products from other manufacturers which speak a non-SDP communication protocol with the medical devices speaking an SDP communication protocol.

Figure 7A:
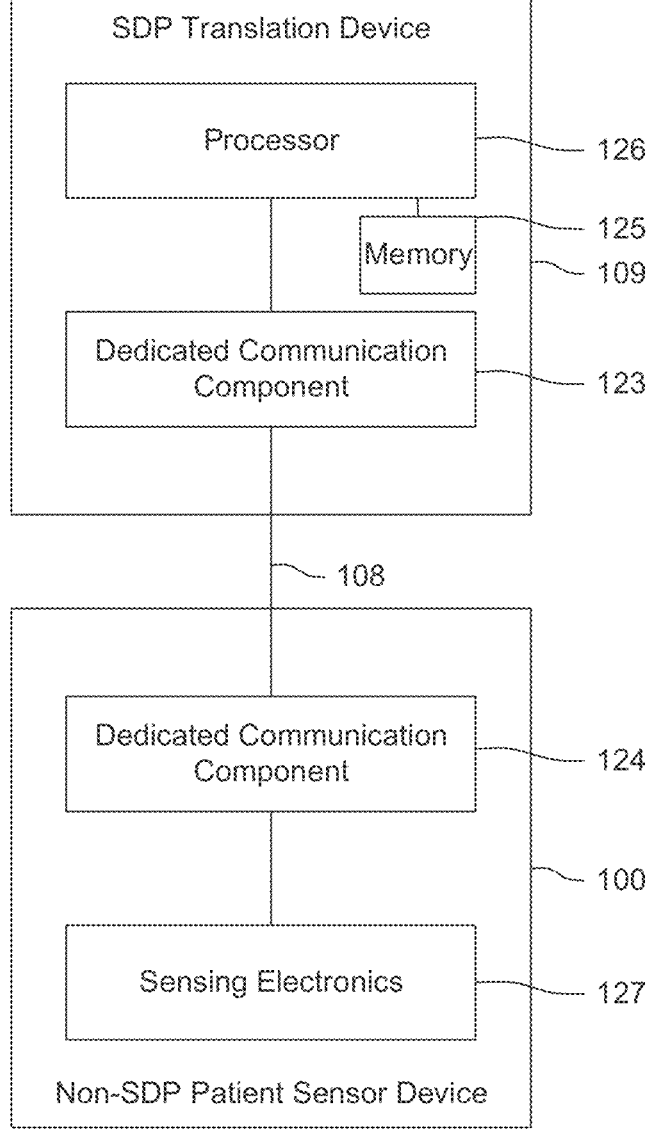
FIG. 7A is a schematic block diagram that illustrates the communication between an SDP translation device and a non-SDP patient sensor device according to one or more embodiments.

FIG. 7A provides a schematic block diagram of a non-SDP patient sensor device 100 in electrical communication via wired or wireless connection 108 to as SDP translation device 109 according to one or more embodiments. The non-SDP patient sensor device 100 comprise sensing electronics 127 that support the physiological parameter being measured on the patient and a communication component, or dedicated communication component 124 (e.g., communication circuitry such as a transmitter or a transceiver), which speaks or provides communication output in a communication protocol that differs from the system or SDP.

The SDP translation device 109 comprises a processor 126 and a dedicated communication component 123 (e.g., communication circuitry such as a receiver or a transceiver) to enable communication with the non-native patient sensor device 100 through its dedicated communication component 124 or other means (not shown). The SDP translation device 109 further includes memory 125 that stores an SDP library that is accessed and read by the processor 126. In some cases, the memory 125 may be embedded in the processor 126.

Figure 17:
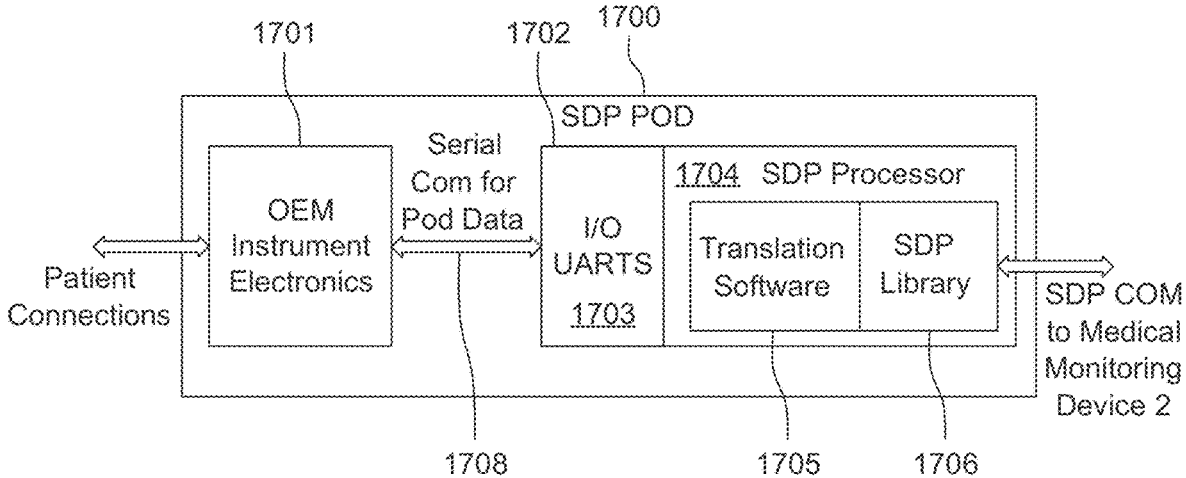
FIG. 17 is an illustrative embodiment of an SDP translation device comprising an SDP processor board within an SDP translation cable or SDP pod that further comprises translation software within the SDP processor board according to one or more embodiments.

The SDP library contains a non-SDP (NSDP) catalog of other communication protocols (e.g., non-SDP communication protocols) that can be translated into the SDP communication protocol. In other words, the NSDP catalog includes a mapping of one or more different communication protocols to the SDP. Using this NSDP catalog, the processor 126 can identify the non-SDP communication protocol used by the non-SDP patient sensor device 100 and extract the mapping information. The processor 126, in turn, uses the mapping information extracted from the SDP library to translate the received non-SDP data into the SDP format for transmission to the input node 113. Said differently, the SDP translating device 109 is configured to identify the non-SDP of the non-SDP sensor data, select an NSDP-to-SDP conversion algorithm from a catalog or collection of NSDP-to-SDP conversion algorithms provided by the SDP library based on the identified NSDPCOM, and translate non-SDP sensor data into SDP sensor data using the selected NSDP-to-SDP conversion algorithm. Translation software illustrated in FIGS. 17 and 21 is used to perform the translation along with the SDP library. In one particular embodiment of FIG. 7A, the dedicated communication components 123 and 124 in SDP translation device 109 and non-native patient sensor device 100 comprise electronic subsystems such as, but not limited to, microprocessors or field-programmable gate arrays (FPGAs). Dedicated communication component 123 and dedicated communication component 124 may be the same electronic subsystems or may be different electronic subsystems. Dedicated communication component 123 exchanges information with an electronic processor 126 in the SDP translation device 109.

Electronic processor 126 is a device such as a microprocessor that is able to execute instructions to implement the translating function using the SDPs library. Dedicated communication component 123 and dedicated communication component 124 exchange information electronically using connection 108 which may be a bi-directional serial link NSDPCOM. The dedicated communication component 124 receives information about a physiological measurement (e.g., physiological sensor data) from the sensing electronics 127 in the non-native patient sensor device 100 through a variety of methods such as, without limitation, digitizing an analog signal or sensing digital signals or similar methods. The dedicated communication component 124 is able to control the operation of sensing electronics 127 using digital or electronic signals.

Examples of the some of the parameters that may be measured on a patient using a non-native or OEM device, translated into SDP using the SDP translation device described herein, and analyzed and displayed on the medical device and system described herein in a spot-check or continuous measurement include the following: oxygen saturation of arterial hemoglobin (SpO2) (e.g., measuring blood oxygen saturation fraction from absorption of light at different wavelengths as it passes through the finger), perfusion index (PI), pulse rate, carboxyhemoglobin saturation (SpCO), methemoglobin (SpMet), total hemoglobin (SpHb), patient volume index (PVI), total oxygen content (SpOC), neuromusculartransmission (NMT, measuring state of anesthesia by electrically stimulating nerves in the hand and measuring the motion response at the fingertip using an accelerometer), bispectral index (BIS, measuring state of anesthesia from induced electrical potentials over the brain), electro encephalogram (EEG), sidestream or mainstream end-tidal C02 (e.g., measuring C02 in sample of exhaled breath or primary exhalation stream of a patient using infrared spectroscopy), anesthetic gas monitoring (e.g., measuring oxygen and anesthetic agent concentrations in a stream of gas inhaled by patient), measurements of cardiac output from invasive blood pressure and temperature measurements and measurements of blood oxygen saturation from an optical sensor coupled by fiber to the tip of a catheter; measurements of blood characteristics using absorption of light at different wavelengths and hemo or hemodynamic module (e.g., measures invasive blood pressures and cardiac output), duplicates (e.g., dual Sp02 or IBP), or any combination thereof. Without limitations, some of the parameters that may be measured on a patient using a non-SDP sensor devices, and further be translated into a SDP communication protocol using the SDP translation device described herein may further include continuous non-invasive arterial pressure, transcutaneous oximetry (TcP02), transcutaneous C02 (TcC02), impedance cardiograph (ICG), glucose monitoring (e.g., continuous glucose monitoring), pupillometry, indirect calorimetry.

The SDP translation device 109 is intended for use in all hospital care areas, during transport between care areas, and in ambulance. In certain embodiments, the SDP translation device 109 operates in one or more of the following conditions: ambient temperature range of from about 0 to about 40° C.; ambient relative humidity range of from about 10% to about 95% (without condensation); and/or ambient air pressure range of from about 620 hPa to 1100 hPa.

In one embodiment, when the SDP translation device 109 is connected with an SDP-speaking medical device (e.g., medical device 2, patient monitor, anesthesia machine, therapeutic device, ventilator), the SDP translation device 109 may receive, from the SDP-speaking medical device, the localization settings of the medical device. The localization settings may include atmospheric conditions (e.g., temperature and pressure), location settings (e.g., geographical locations, specific clinic sites, or care areas). For example, when the SDP translation device 109 is connected with a patient monitor located in a pediatric unit, the SDP translation device 109 may adjust alarm limits and other configuration settings accordingly, upon receipt of the localization settings for the pediatric unit. Some of the non-SDP sensor devices (e.g., gas detecting sensors) need calibration process or adjustment based on the temperature and/or pressure of the current location. When these non-SDP sensor devices are connected, via the SDP translation device 109, to the medical device 2, the medical device 2 may measure atmospheric pressure using internal sensors and provide the information to other non-SDP sensor devices via the SDP translation device 109, or to other devices (e.g., the network of medical computing devices 104) as part of the context data.

Alternatively, or additionally, when the SDP transition device 109 adjusts settings, it may request user input via a user interface of the SDP-speaking medical device (e.g., notifications or request for users to accept a configuration change).

Figure 7B:
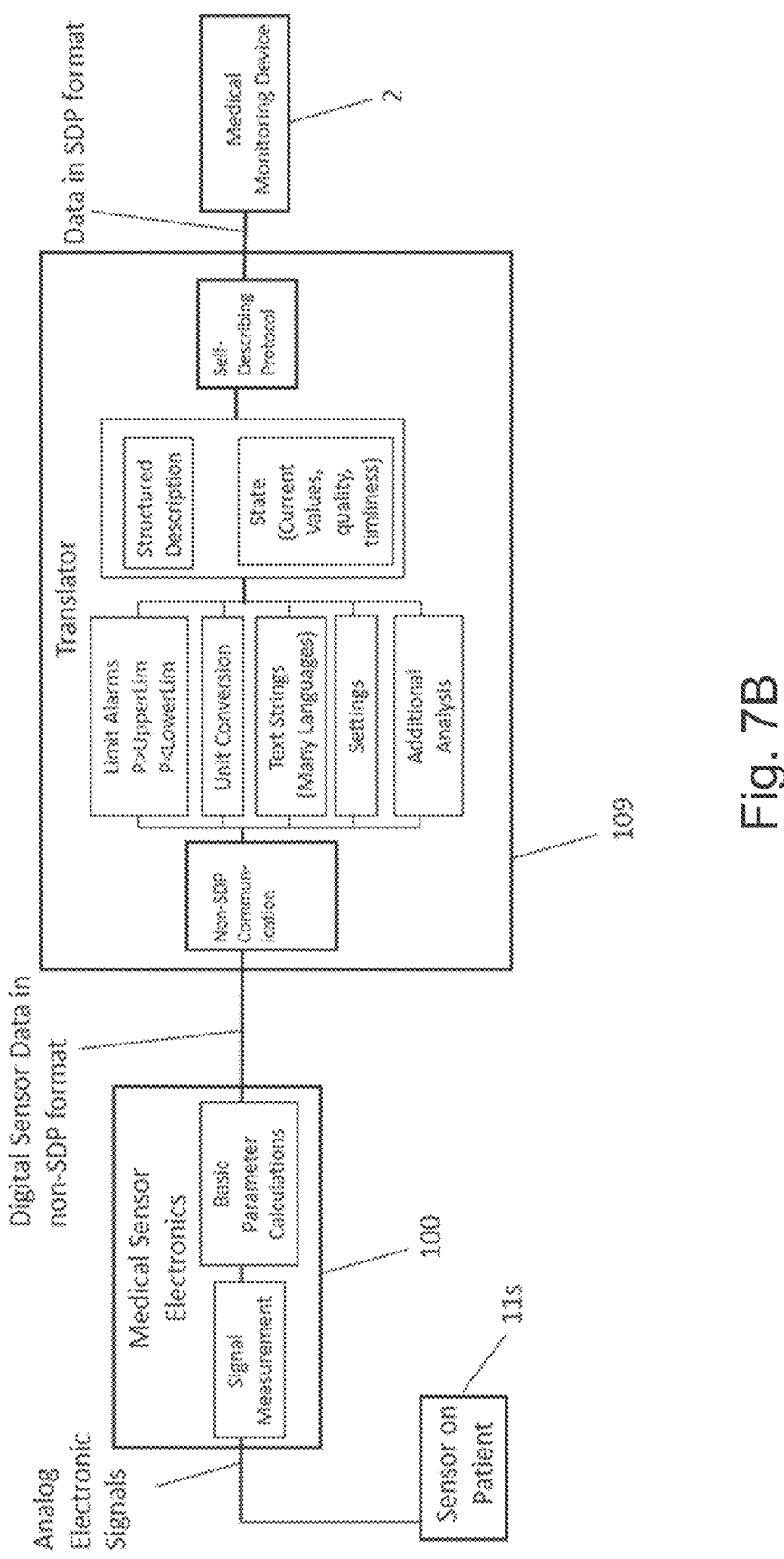
FIG. 7B is a schematic block diagram of a system according to one or more embodiments.

FIG. 7B is a schematic block diagram of a system 700 according to one or more embodiments. The system 700 is similar to that of system 600 but shows the non-SDP patient sensor device 100 and the SDP translation device 109 in greater detail. A sensor 11s is attached to, interfaced with, or otherwise engaged with a patient 11 (not illustrated) in order to obtain measurements of a patient parameter and transmit analog electronic signals to the non-SDP patient sensor device 100 representative of the measurements.

The electronics of the non-SDP patient sensor device 100, for example, processing circuitry including an analog-to-digital converter and signal processing circuitry, performs signal measurements and basic parameter calculations in order to generate digital sensor data having a non-SDP format. The digital sensor data (e.g., physiological parameters) are transmitted by the non-SDP patient sensor device 100 to the SDP translation device 109 using a non-SDP communication protocol. The transmission of the digital sensor data may be made via a wired or a wireless communication link.

FIB. 7B shows the transfer and enhancement of physiological measurement data between a sensor 11s on a patient and a multi-function medical device 2 (e.g., a patient monitor). A sensor 11s on patient produces an electronic measurement that is detected by signal measurement electronics in a non-SDP medical device 100. Processing circuitry (e.g., a microprocessor and/or DSP) of the non-SDP medical device 100 uses software to perform basic parameter calculations on the measured signal data to produce clinically-relevant quantities (e.g., digital sensor data such as patient physiological data) that are reported by electronic means such as a digital serial signal over a wire or a wireless transmission to the SDP translation device 109.

The SDP translation device 109, via processor 126 for example, enhances the value of the clinically-relevant quantities by performing functions such as, the NSDP-to-SDP translation function, as well as testing the clinically-relevant quantities against limits and producing additional alarm event signaling information that indicates an alarm and/or can be used by the medical device 2 to generate alarms to draw attention of caregivers, changing the units of measure of the quantities to units most meaningful to caregivers and most usable to the medical device 2 for the handling and processing thereof, providing descriptive text strings to characterize the quantities in one or more languages (e.g., English, German, Chinese, etc.), providing settings that permit changes to the way the quantities are processed by the medical device 2, access to those settings being provided by communication with one or more devices external to the SDP translation device 109, further processing of the quantities by algorithms that use features such as temporal changes to the quantities or mathematical calculations involving at least one of the quantities and other values such as other quantities received from the non-SDP medical device 100 or quantities obtained by the SDP translation device 109 from sources internal or external to the SDP translation device 109, or other enhancements that increase the clinical utility of the quantities, or a plurality of these enhancements. This addenda information, including additional signaling information, units of measure information, descriptive text strings, settings information, access information, and the like may be attached to or transmitted with the translated SDP sensor data (e.g., in a same data structure, such as the MDB) that the SDP translation device 109 transmits to the medical monitoring device 2.

Figure 7C:
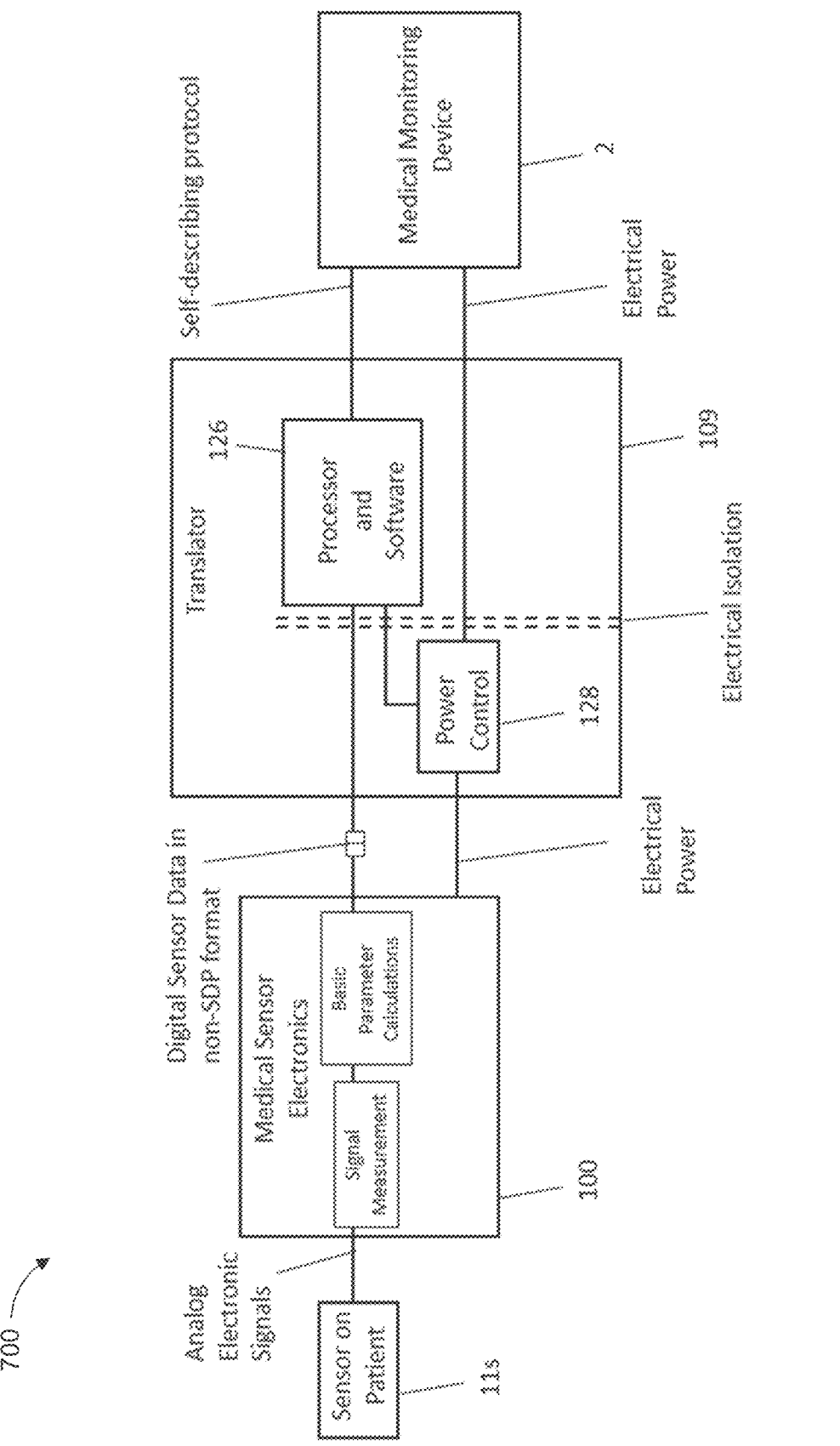
FIG. 7C depicts another schematic view of the system shown in FIG. 7B according to one or more embodiments.

The SDP translation device 109 arranges the quantities in the enhanced form and other information resulting from the enhancements in a data structure that is defined within the SDP and that may include characterizations of elements of the data structure or operating characteristics of the SDP translation device 109 or the non-SDP medical device 100 using characteristic codes defined within the SDP. The SDP translation device 109 transmits the data structure to another device such as the medical device 2 in a manner prescribed by the SDP and may report changes to all or part of the data structure at regular or irregular time intervals. The SDP translation device 109 may receive communications of pre-scribed changes to the data structure from another device such as the medical device 2 in a manner prescribed by the SDP and may receive prescribed changes to all or part of the data structure at regular or irregular time intervals. FIG. 7C depicts another schematic view of system 700 according to one or more embodiments. Here, the SDP translation device 109 also provides electrical isolation between the medical device 2 (e.g., a patient monitor) and the non-SDP patient sensor device 100 to protect the patient. For example, the medical device 2 supplies electrical power to the SDP translation device 109 and the SDP translation device 109 supplies electrical power to the non-SDP patient sensor device 100.

For example, the SDP translation device 109 may include a power controller 128 that receives electrical power from the medical device 2 and controls the distribution thereof to the processor 126 and to the non-SDP patient sensor device 100. In particular, the power controller 128 may include a voltage regulator that generates a supply voltage for the non-SDP patient sensor device 100 that is the same or different from the voltage provided to the SDP translation device 109 and the processor 126 thereof.

The SDP translation device 109 may further include an electrical isolation barrier that provides isolation between two different electrical domains, which may be different voltage domains. For example, the processor 126 may reside in a first electrical domain and the non-SDP patient sensor device 100 and the sensor 11s may reside in a second electrical domain. Thus, the electrical isolation barrier may protect both the non-SDP patient sensor device 100 and the patient 11. Alternatively, the processor 126 may reside in the second electrical domain, electrically isolated from the medical device 2.

The power controller 128 may also limit an amount of current supplied to the non-SDP patient sensor device 100, and is configured to turn power to the non-SDP patient sensor device 100 on or off.

Figure 8:
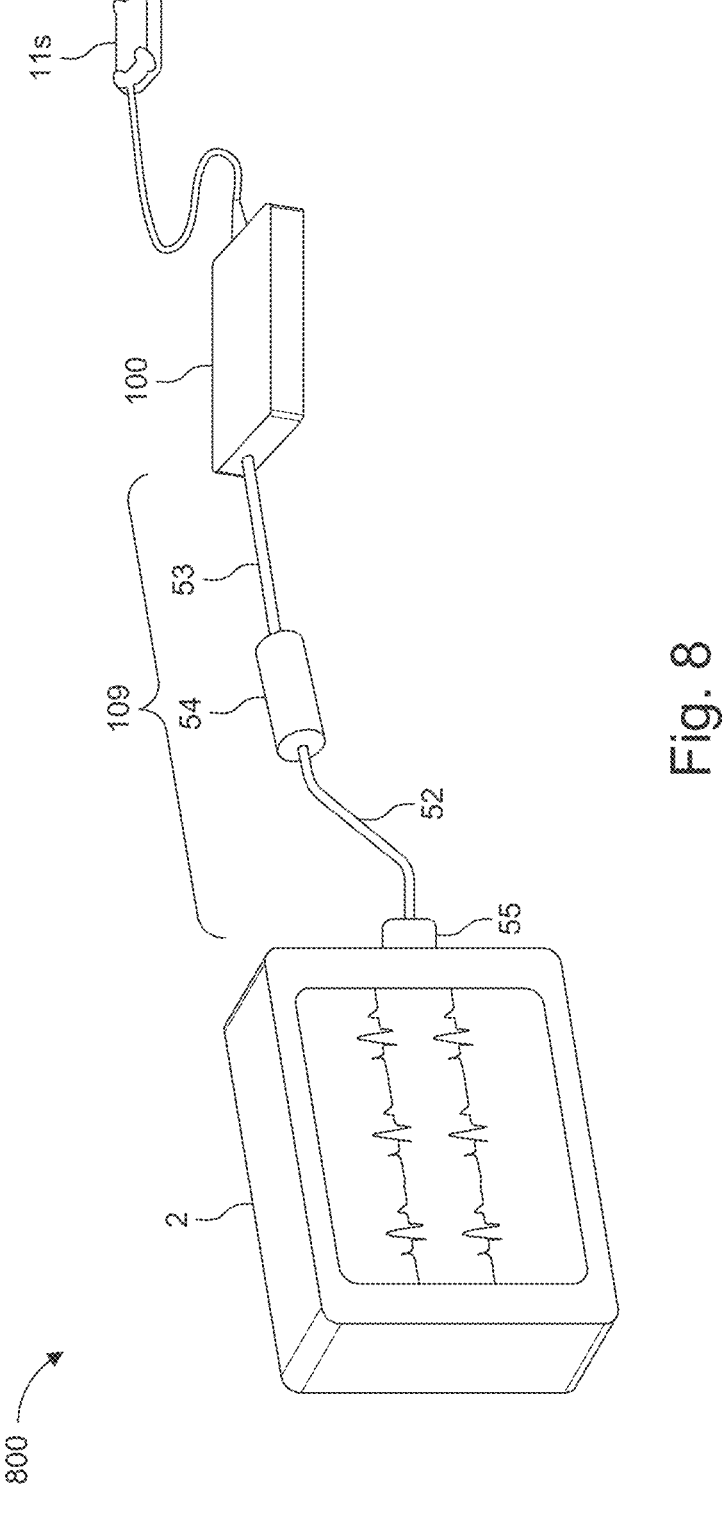
FIG. 8 illustrates a system that comprises an SDP translation device in a cable form and is interposed between a medical device and a non-SDP patient sensor device according to one or more embodiments.

FIG. 8 shows an example of a system 800 comprising an SDP translation device 109 according to one or more embodiments. In this example, the SDP translation device 109 is illustrated as a SDP translation cable, which is in communication with a non-native device such as non-SDP patient sensor device 100. The system 800 further includes an attached sensor 11s that transduces physiological quantities measured at the patient to electronic signals. The system 800 further includes the medical device 2 as an input node of the SDP communication network. The SDP translation device 109 includes an SDP translator 54 that houses the dedicated communication component 123, the processor 126, and any associated memory 125. The SDP translator 54 is configured to convert or translate the data of the non-SDP communication protocol to the SDP communication protocol (i.e., the SDP) using the SDP library.

The SDP translation device 109 further includes optional electrical cables 52 and 53, where electrical cable 52 is configured to connect the SDP translation device 109 to the medical device 2 and electrical cable 52 is configured to connect the SDP translation device 109 to the non-SDP patient sensor device 100. Additionally, the SDP translator cable 109 may include a connector 55 that is configured to connect to and establish a communication connection with a medical device 2. Accordingly, the SDP translation device 109 is in communication with the non-SDP patient sensor device 100 and the medical device 2 via electrical cables 52 and 53 in this example.

Figures 9A, 9B:
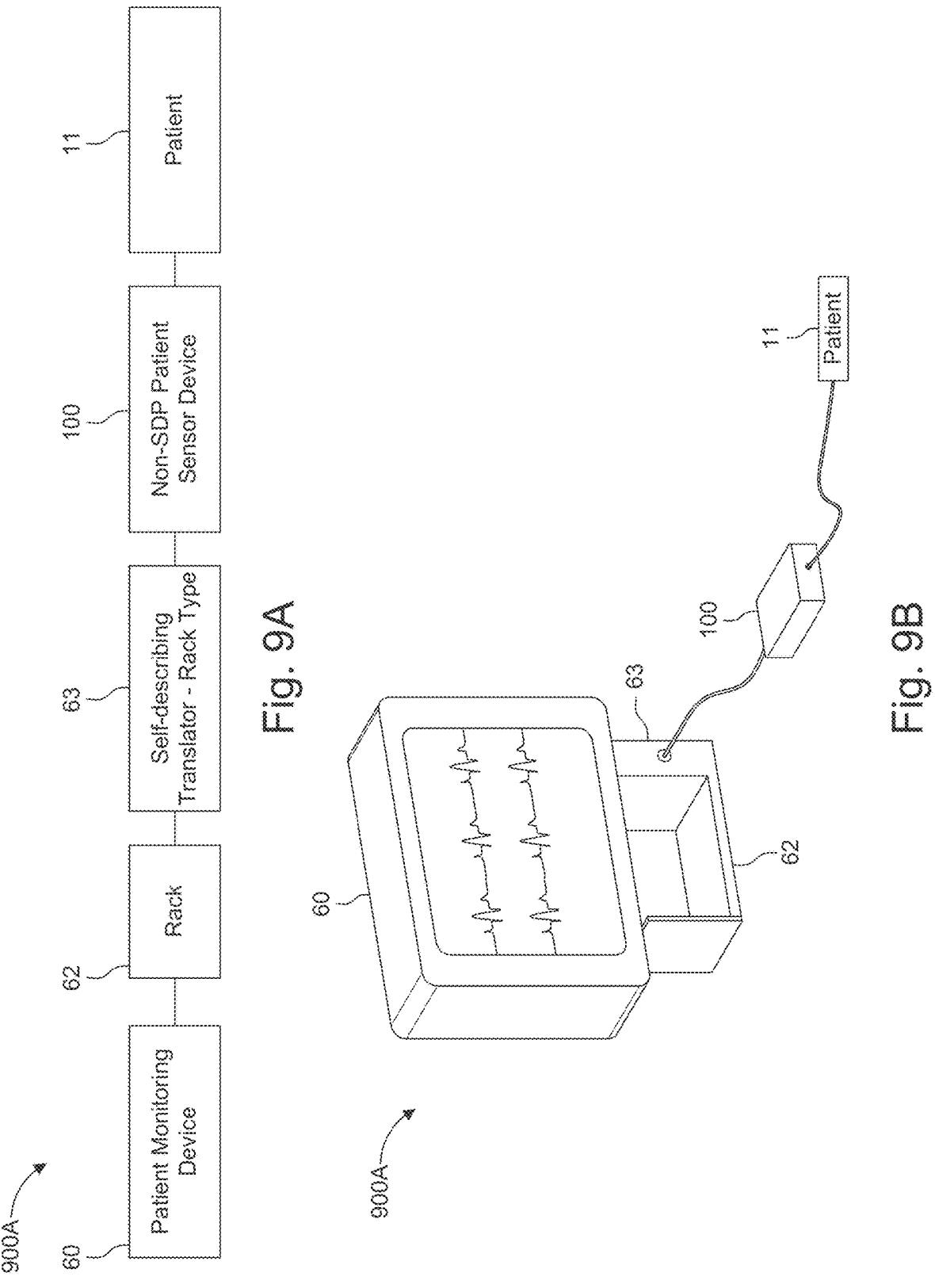
FIG. 9A and FIG. 9B illustrates a system that comprises a translation device that is in a mounting rack and communicates with a non-SDP patient sensor device according to one or more embodiments in both a block form and in schematic form, respectively.

FIGS. 9A and 9B show a rack-based embodiment of a translator system 900A. In this embodiment, the SDP translation device is a rack-type self-describing translation device 63 that is enclosed in a rack module 62 that connects the translation device 63 to an embodiment of the medical device 2 which is depicted in FIGS. 9A and 9B as a patient monitoring device 60. The non-SDP patient sensor device 100 is also connected to the patient 11, for example, via one or more sensors. The various components in FIGS. 9A and 9B are in electrical communication with each other. The rack-type self-describing translation device 63 performs all the same functions described above with respect to the SDP translation device 109. For example, the rack-type self-describing translation device 63 translates data from a non-SDP protocol to an SDP protocol and provides a data enhancing functions as described in FIG. 7B.

Figure 9C:
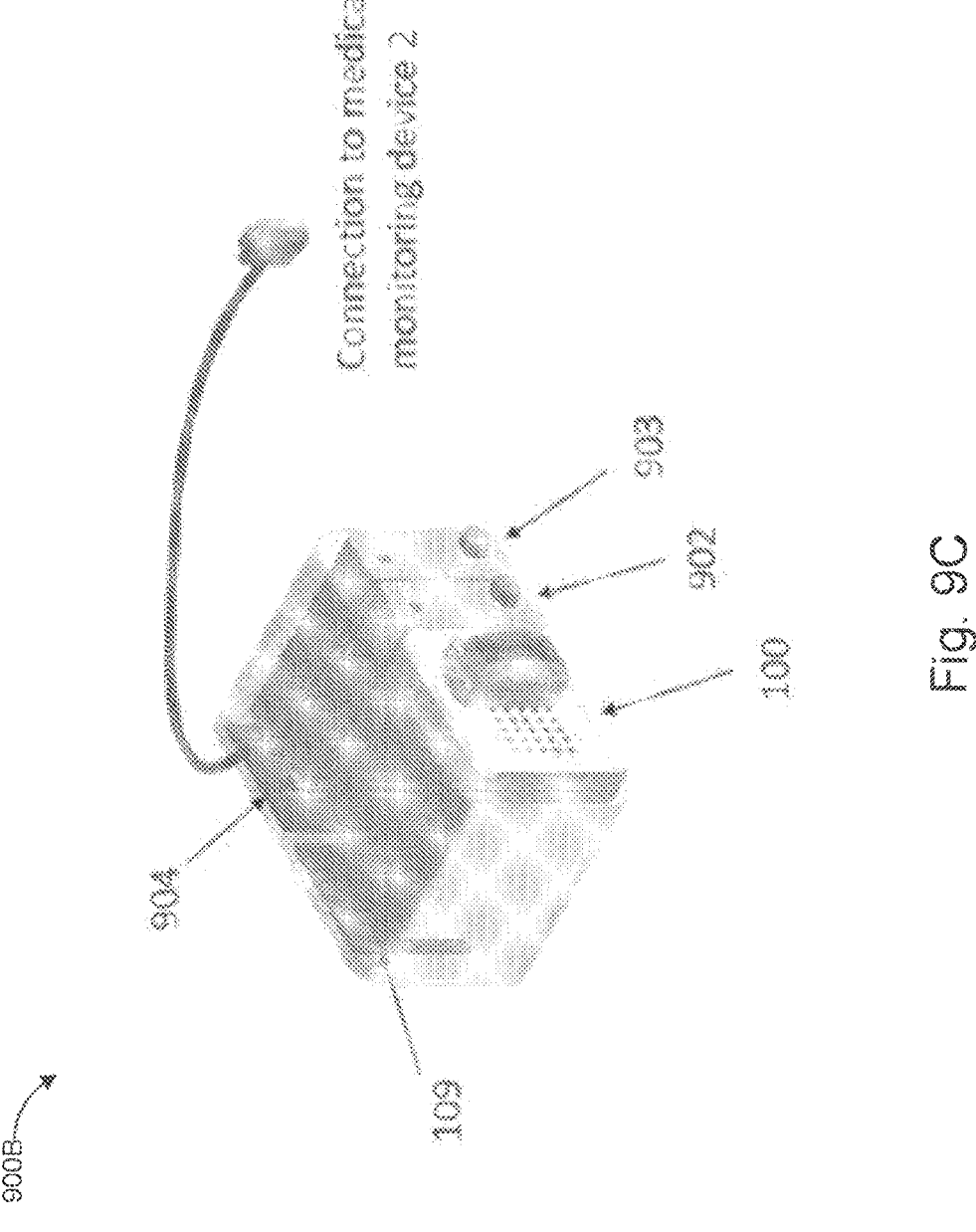
FIG. 9C shows an example of a medical device according to one or more embodiments.

FIG. 9C shows an example of a medical device 900B according to one or more embodiments. The medical device 900B comprises an enclosure (i.e., a housing) and at least one non-SDP medical device 100 arranged in the enclosure. The medical device 900B optionally comprises one or more self-describing modules 902 and 903 (e.g., self-describing patient sensor devices) arranged in the enclosure, each configured to provide data according to an SDP. The medical device 900B further comprise at least one SDP translation device 109 (e.g., an SDP translation board) that provides a means of communicating data between the non-SDP medical device 100 and another device such as a medical device 2 that requires connected devices to employ a defined SDP. Data from all of the devices may be provided together or in pieces from one device or more devices contained in the enclosure 901 to the medical device 2.

For example, the self-describing medical devices 902 and 903 may communicate with and exchange SDP data directly with the medical device 2 through a communication interface 904. In contrast, the non-SDP medical device 100 may only communicate with and exchange data with the medical device 2 via the SDP translation device 109, which receives non-SDP data from the non-SDP medical device 100, translates the non-SDP data into SDP data, and transmits the SDP data to the medical device 2.

Figure 10:
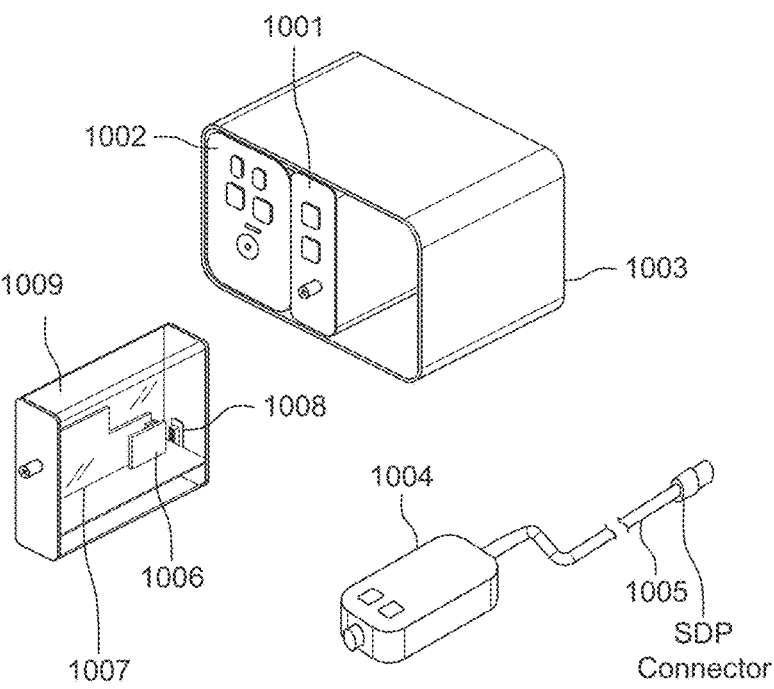
FIG. 10 is a schematic diagram of various embodiments of self-describing or natively speaking SDP modules having a single width and a double width, a mounting rack for the self-describing modules, and a tethered module which does not reside in the mounting rack and is connected to the rack via a cable.

FIG. 10 is a schematic diagram of a mounting rack 1003 configured to house one or more devices according to one or more embodiments. The mounting rack 1003 is similar to medical device 900B in that the mounting rack 1003 has an enclosure configured to house one or more self-describing modules 1001 and 1002 that transmit data in the SDP format. The self-describing module 1001 has a single-width form factor and the self-describing module 1002 has a double width form factor. Thus, self-describing or SDP natively speaking modules may be mounted within a rack 1003 such as that shown in FIG. 10.

In one embodiment, an SDP translation module 1009 is implemented as the SDP translation device and may be inserted into a corresponding slot or volume of the SDP rack 1003. The SDP translation module 1009 may be a sensor device with SDP translation functionality or may be connected to or otherwise interface with a non-SDP medical device 100 that may itself be inserted into the rack 1003 or arranged external thereto.

The SDP translation module 1009 is provided with and therefore includes a Software Development Kit (SDK) that includes the SDP library. This SDP library can be used on an embedded processor that could be part of an existing interface board 1006 from a third party (which has received the SDK and uploaded the SDP library in advance) or could be located on a separate SDP processor board shown in FIGS. 17 and 21 or such as the dedicated communication component 123 shown in FIG. 7A.

The SDP processor board 1006 may further comprise a USB interface 1008 to the host for SDP communication as well as serial interfaces to communicate with the OEM parameter board 1007 using its existing command set for measuring a physiological parameter. The SDP processor board 1006 has an interface and transmits its measurements as requested through a proprietary command set. The product can be converted to an SDP device by connecting the port of the non-SDP patient sensor device to the SDP translation device 109. The SDP translation device 109 communicates with the SDP processor board 1006 (such as the dedicated communication component 124 in FIG. 7A) of non-SDP patient sensor device to obtain measurements, perform additional processing, tests alarm limits if appropriate, sends the data to the medical device through the SDP library, or combinations thereof.

Figures 11A, 11B, 11C, 11D:
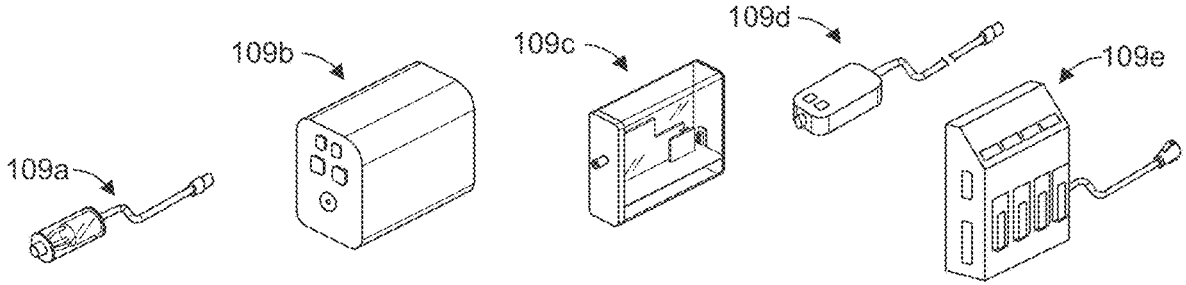
FIGS. 11A-11D show various types of SDP translation devices according to one or more embodiments.

FIGS. 11A-11D show various types of SDP translation devices 109a, 109b, 109c, 109d, and 109e according to one or more embodiments. The SDP translation device 109a depicted in FIG. 11A is an SDP translator cable, the SDP translation device 109b depicted in FIG. 11B is an SDP double-width rack pod, the SDP translation device 109c depicted in FIG. 11C is an SDP single-width rack pod, and the SDP translation devices 109d and 109e depicted in FIG. 11D are tethered pods, which have a cable for connecting to patient monitor such as a module with input amplifiers that require cables with limited impedance.

Figure 12:
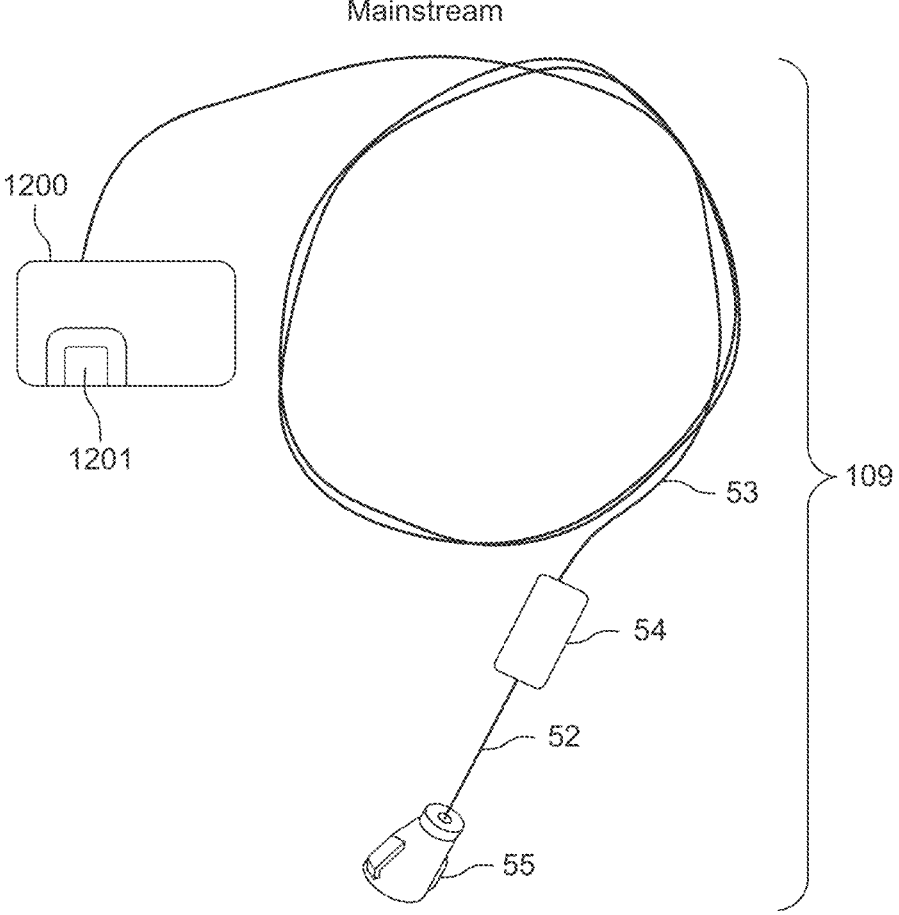
FIG. 12 provides an embodiment of a translation device for gas measurement for end stream C02 for inhaled and exhaled gases.
Figure 13:
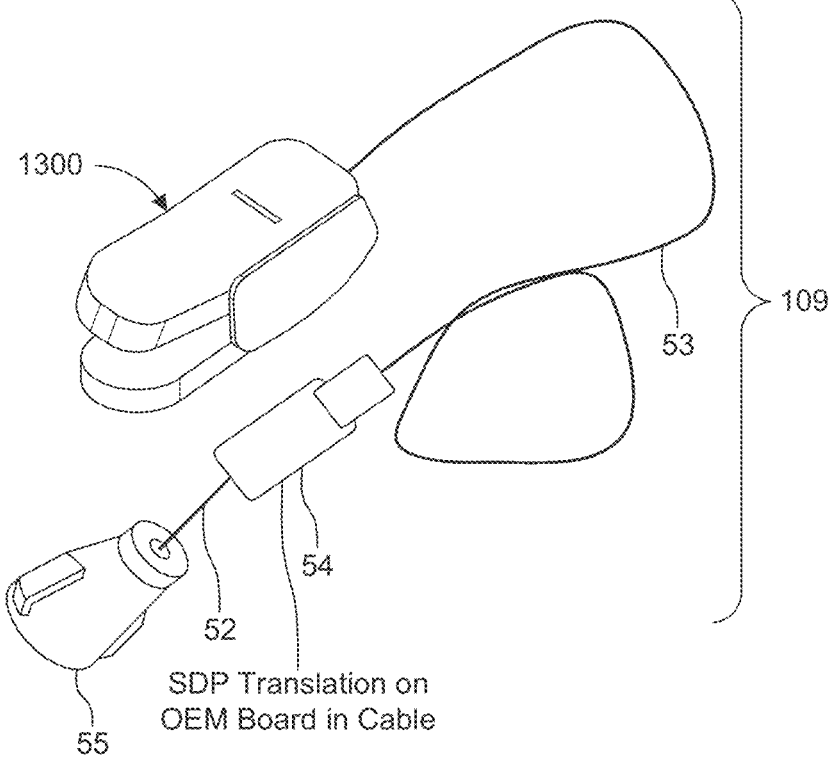
FIG. 13 provides an embodiment of a translation device comprising a translation module integrated in a cable solution (e.g., a self-describing protocol (SDP) internal translator cable) for blood oxygenation or Sp02.

FIGS. 12 and 13 illustrate non-SDP sensor devices that measure concentrations of gases in the respired stream, with each sensor device being incorporated with an SDP translation device. FIG. 12 illustrates a capnography sensor device 1200 with an airway 1201, for detecting end-tidal C02 using infrared spectroscopy. The sensor device 1200 is configured to be connected with an SDP translation cable 109. FIG. 13 illustrates a Sp02 sensor 1300 for measuring oxygen saturation, with the Sp02 sensor configured to be connected with an SDP translator cable 109.

As illustrated in FIG. 12, the sensor device 1200 is connected to or includes an SDP translation device (e.g., an SDP translator cable 109). The SDP translator cable 109 includes a module 54 with an SDP translation serial board within the cable. The SDP translator cable 109 may further include a connector 55 that is configured to connect to and establish a communication connection with a medical device 2. Without limiting the scope of the present disclosure, the SDP translation device that is connected to or be included in the sensor device can be of different sizes and/or forms as described above.

It should also be noted that FIG. 12 illustrating a mainstream C02 sensor applied to the primary exhalation stream is for exemplary purposes only. The types of non-SDP gas detecting sensors that are communicatively coupled to SDP translation devices should not be limited herein. For example, a microstream C02 sensor which extracts a small fraction of the flow and measures it at a location away from the patient can also incorporated with an SDP translation device in accordance with the present disclosure. Optionally, the microstream C02 device may further include a pump to drive extraction of the sample stream, in addition to the sensors and electronics. A microstream C02 sensor minimizes the size of the hardware that is present around the patient's face, but is one type of capnography preferred to be used on infants because their mainstream flow volume is very low.

In another embodiment, other types of non-SDP gas detecting sensors may also be connected, via an SDP translation device, to medical device 2. For example, a gas detecting sensor may include an infrared sensing unit that measures the concentrations of anesthetic agents (e.g., isoflurane, desflurane, halothane, sevoflurane, and enflurane) in a mix of gasses, which can be used by an anesthesiologist to maintain safe and effective anesthetic conditions for the patient in surgery. Optionally, a gas detecting sensor may incorporate a magnetic sensor to detect oxygen, where a magnetic field is generated by a set of coils within the sensor to measure oxygen concentration in the gas stream. It exploits the paramagnet susceptibility of oxygen to alter the thermal behavior of the gas, which is then measured by electronically detecting temperature changes in the neighborhood of a heating element.

The abovementioned non-SDP gas detecting sensors may be connected to or include in the SDP translation device (e.g., SDP translator cable or SDP translation devices with different sizes and/or forms). As such, these sensors are allowed to be communicatively coupled with medical devices even when these medical devices speak in a different communication protocol from the sensors.

In the event that the C02 device 1200 includes an SDP translator board, the SDP translator board may be housed in a double-width enclosure for the SDP rack 1003, 62. In one particular embodiment, the C02 device will draw up to 16 W for 5 minutes during its warm-up period and thereafter require 7 W. The SDP rack 1003, 62 and monitoring device mount will provide 24V at up to 1 A (24 W) and 5V at up to 1 A to SDP compatible devices. The device will be powered from the 24V supply. To eliminate the need for a 24V/5V convertor on the SDP translator serial board, the translator will be powered from the 5V supply. Some gas measurements require an atmospheric pressure value to correctly reduce their data FIG. 13 provides an illustration of a non-SDP device (e.g., an OEM device) that is used to measure the fraction of hemoglobin in blood that is carrying oxygen which is saturation pressure or Sp02. In particular, a non-SDP Sp02 device 1300 is shown. The Sp02 device 1300 is connected to or includes a translation device (e.g., SDP translator cable 109) and consists of a module 54 with an SDP translation serial board within the cable 109.

The measurement is made by passing red and infrared light through a tissue of interest. Oxygenated and deoxygenated hemoglobin absorb the red and infrared light differently (that is, hemoglobin changes color when it binds oxygen). The measurement can be made in transmission mode by putting the light source and detectors on opposite sides of a tissue sample (e.g., a sensor that clamps lightly to a finger as illustrated), or it can be made in reflectance mode wherein light penetrates the tissue and is reflected back out, passing through the tissue sample in both directions. This measurement is used primarily to measure respiratory function.

Figure 14:
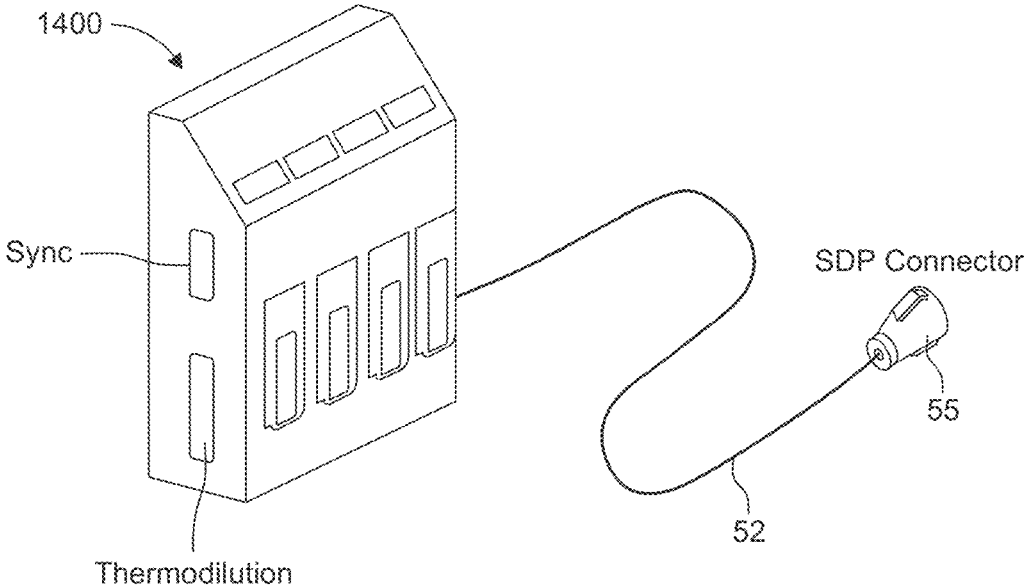
FIG. 14 provides an example of an Invasive Blood Pressure (IBP) hemodynamic device that becomes a self-describing device when using an SDP translation device according one or more embodiments.

FIG. 14 provides an example embodiment of an hemodynamic device 1400 that becomes a self-describing device when using an SDP translation device such as an SDP translation device 109. The hemodynamic device 1400 may comprise an internal SDP translator device or cable for protocol translation. The hemodynamic device 1400 further provides space for up to four invasive blood pressure (IBP) sensors in its enclosure and display information corresponding to each IBP sensor. The SDP hemodynamic devices measure invasive blood pressures and cardiac output. Invasive pressures are measured by a pressure transducer connected to a catheter; the other end of the catheter placed at the measurement point. Cardiac output is measured through thermodilution—a process by which cold saline is injected into the bloodstream and the temperature at another point is used to assess transport of blood.

Through the various embodiments described herein, it will be readily apparent that the SDP translation device 109 can be implemented in many ways, including being integrated with the non-SDP patient sensor device 100 in the same housing as the non-SDP medical sensor electronics and a non-SDP processor. Here, an SDP translation board may be incorporated or otherwise inserted into the non-SDP patient sensor device 100 that serves as an interface between the non-SDP electronics of the non-SDP patient sensor device 100 and an SDP speaking multifunction medical device. The SDP translation board receives non-SDP sensor data, translates the sensor data into the SDP format with enriched data, and the non-SDP patient sensor device 100 transmits SDP formatted data to the multi-function medical device (e.g., medical device 2) with the assistance of the SDP translation board. Alternatively, the SDP translation device 109 can be provided external to the SDP patient sensor device 100 in the form of an SDP translation module, SDP translator cable, or the like. Regardless of the implementation, the SDP translation device 109 performs a similar function in that it interfaces between the non-SDP patient sensor device 100, or the non-SDP circuitry thereof, and the SDP multi-function medical device in order to translate non-SDP sensor data into an SDP format that can be optimized for and used by the SDP multi-function medical device.

Figure 15:
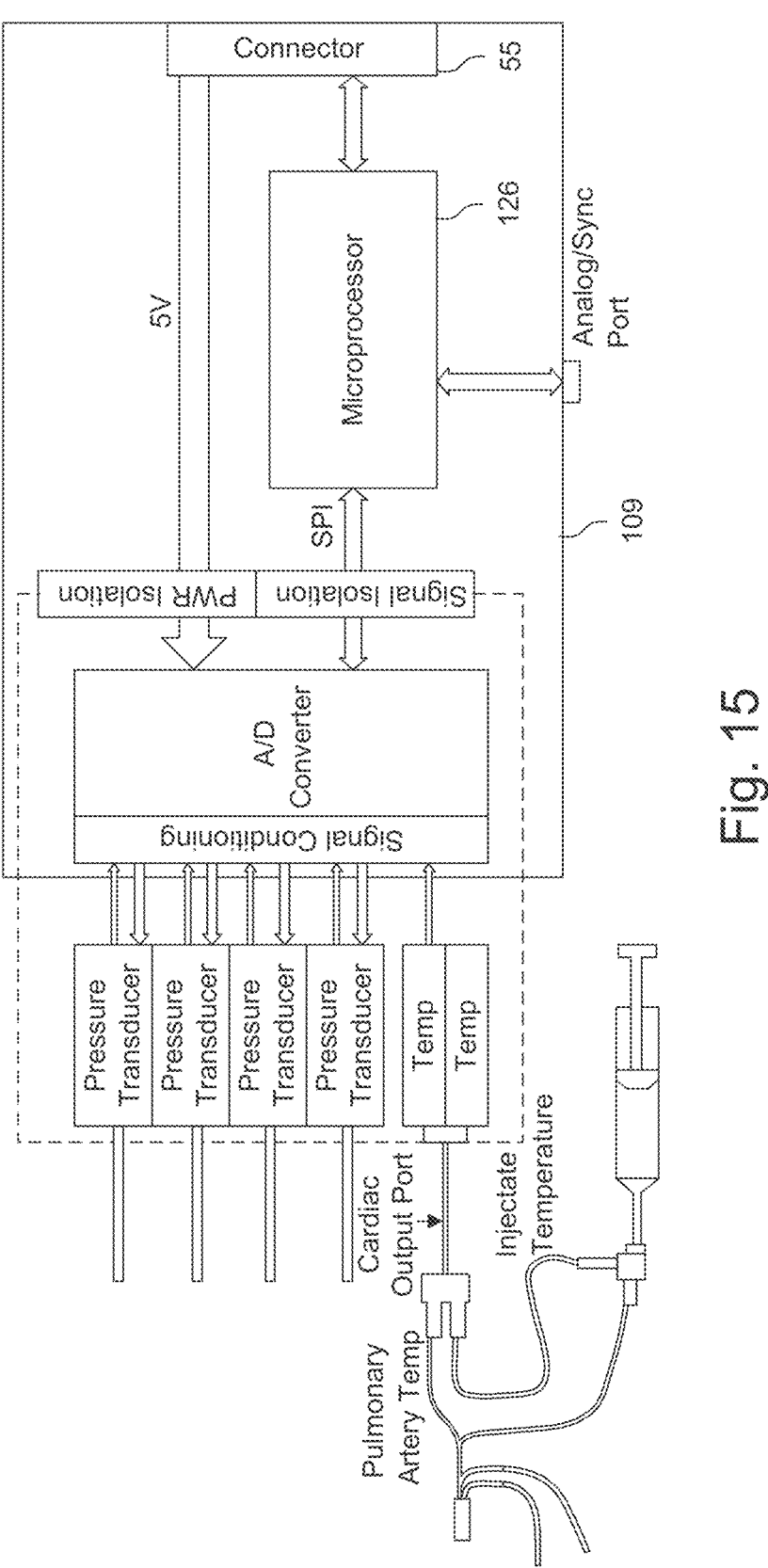
FIG. 15 provides a more detailed, block diagram of an embodiment of an SDP translation device and a device for certain physiological parameter measurements.

FIG. 15 shows the block diagram for the hemodynamic device incorporated with SDP translation device 109. The device further uses accessories to measure cardiac output (the pulmonary artery catheter, temperature probes, and y-cable for temperature). In the embodiment shown, the analog section (isolators, signal conditioners, and A/D converters) is identical to the temp/IBP section on the medical device's analog front-end.

As previously mentioned, the SDP translation device 109 further comprises a connector 55 that allows it to be connected to a medical device 2, a module, or other component within the system. In this embodiment, the connector 55 is integrated with the SDP translator 54 that comprises SDP processor 126 (microprocessor) and the SDP library. As a result, electrical cable 52 is not present. The connector 55 may be male or female. On the opposing end of the SDP translation device 109 from connector 55, a non-SDP sensor 100 may be connected to provide non-SDP sensor data to the SDP translation device 109.

Figure 16A:
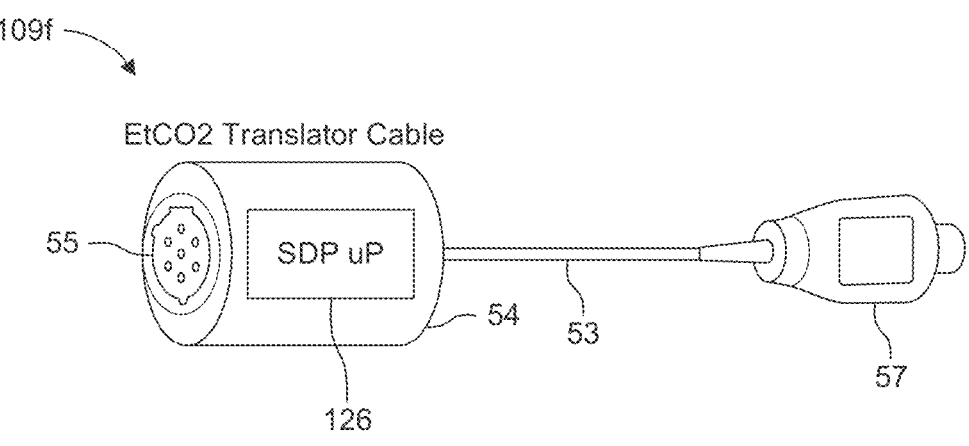
FIGS. 16A, 16B, and 16C illustrate various types of SDP translator cables according to one or more embodiments
Figure 16B:
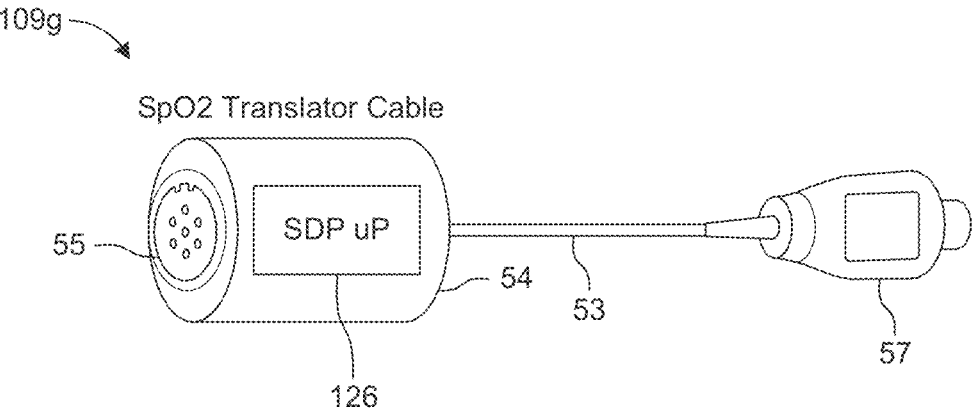
Figure 16C:
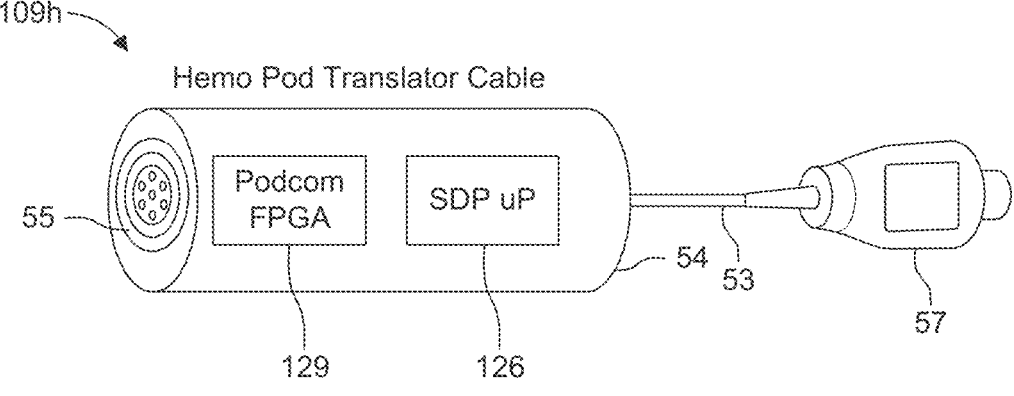

FIGS. 16A, 16B, and 16C illustrate various types of SDP translator cables 1091, 109g, and 109h, respectively, according to one or more embodiments. Each of the SDP translator cables 109f, 109g, and 109h include an SDP translator module 54 that includes an SDP microprocessor uP that is configured to translate non-SDP data into SDP data in accordance with the disclosure provided herein (e.g., via software and cross-referencing an SDP library stored in memory 125 (not illustrated). The translator cables 109f, 109g, and 109h further include a second connector 57 that is configured to be connected to a non-SDP patient sensor device 100 for receiving non-SDP sensor data therefrom and optionally supplying power to the non-SDP patient sensor device 100 through one or more connector pins. The connector 57 is female on one side to connect to a non-native device and male on the other side at connector 55. However, either connector 55 and 57 could be male or female.

In one example, the SDP translation devices 109f, 109g, and 109h depicted in FIGS. 16A-16C are to be connected to non-SDP sensor devices to measure end-tidal C02, SpO2, and hemo or hemodynamic module, respectively. In the embodiments shown in FIGS. 16A-16C, the SDP translation devices 109a, 109b, and 109c comprise an SDP processor (e.g., a microprocessor uP) and the SDP translation device for hemodynamic device may further comprise a field-programmable gate array 129.

Figure 18:
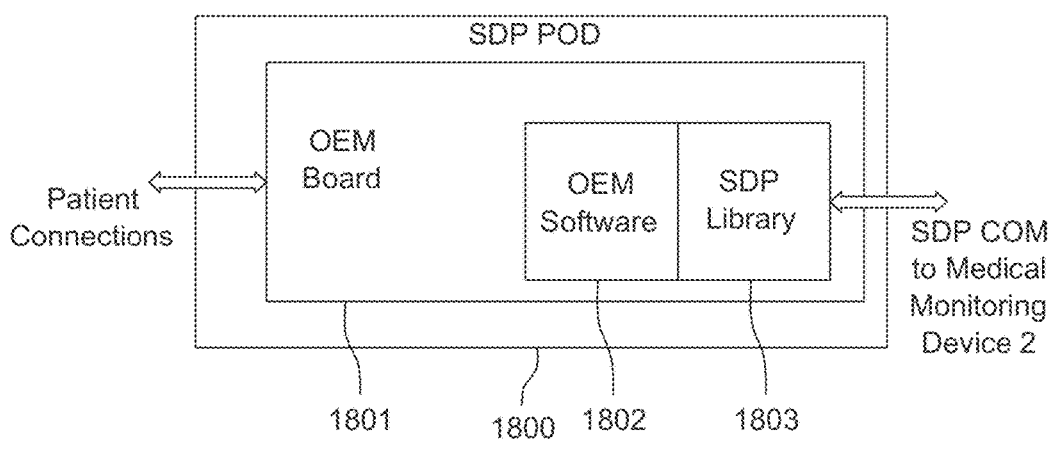
FIG. 18 is an illustrative embodiment of an SDP translation device comprising an SDP processor board within an SDP translation cable or SDP pod that further comprises translation software on a third party, OEM, or non-native processor board.

FIGS. 17 and 18 provide illustrations of different embodiments of a serial protocol for SDP communication using an SDP processing board, as shown in FIG. 17, or an OEM board having the translation software installed in the OEM software and an SDP library also installed in memory. Each embodiment has instrumentation electronics and software specific to the device, an SDP communications (SDP-COM) interface library, or SDP library for short, and an intermediate software unit that creates and maintains the description and state structures in the MDIB by calling the SDP-COM interface library functions.

In FIG. 17, a schematic diagram of an SDP pod 1700 as one example of SDP translation device is shown. The SDP pod 1700 includes OEM instrument electronics 1701 that interface with one or more sensors 11s. The OEM instrument electronics 1701 transmits physiological measurements, sensor data, and the like in the form of serial communication data 1708 to an I/O universal asynchronous receiver-transmitter (UART) 1703 of an SDP translator 1702. The SDP translator 1702 may be an SDP serial board that includes an SDP processor 1704 that is configured in a similar manner as translator module 54 and performs similar functions described above in reference to processor 126 and the dedication communication component 123. Accordingly, the SDP processor 1704 includes SDP translation software 1705 and an SDP library 1706, both stored in memory. The SDP processor 1704 (i.e., a processor board) is connected to an existing non-SDP device (i.e., a non-native device) with a serial interface.

The SDP processor 1704 is configured to execute the translation software 1705 and the SDP library 1706, to convert the communication data 1708 (e.g., non-SDP digital sensor data) from its non-SDP (non-native) communication protocol (NSDPCOM) into the SDP communication protocol (SDPCOM). In particular, the SDP processor 1704 uses the translation software 1705 and the SDP library 1706 to identify the type of the non-native, non-SDP communication protocol being utilized for the communication data 1708, to determine an NSDP-to-SDP conversion algorithm in the SDP library 1706 based on a mapping of the identified non-SDP communication protocol, and to convert the non-SDP data into the SDP based on the determined NSDP-to-SDP conversion algorithm SDP. The assembly of the SDP pod 1700 can be housed in an SDP rack device or in another form factor.

In FIG. 18, a schematic diagram of an SDP pod 1800 as one example of SDP translation device is shown. The SDP pod 1800 having the SDP software integrated with the OEM instrument electronics and OEM software 1802 on a single board. The OEM board 1801 is a processing board and the OEM software incorporates the translation software (e.g., translation software 1705 therein). Accordingly, a processor of the OEM board 1801 is configured to execute the OEM software, and additionally the translation software, which refers to the SDP library 1803, to convert communication data (e.g., non-SDP digital sensor data) from its non-SDP communication protocol (NSDPCOM) to the SDP communication protocol (SDPCOM). In particular, the OEM processor uses the translation software to identify the type of the non-SDP communication protocol being utilized for the communication data, to determine a conversion algorithm in the SDP library 1803 based on a mapping of the identified non-SDP communication protocol, and to convert the non-SDP communication data into the SDPSDP based on the determined conversion algorithm.

The choice of configurations depends on factors such as the nature of the pod, whether the onboard processor has the capacity to support the instrumentation software and the SDP communication operation, whether feasibility of an SDP-specific board design.

The SDP library 1803 is intended to be platform-independent, and/or if the development is being performed on a board comprising a microprocessor such as the one shown.

Figure 19:
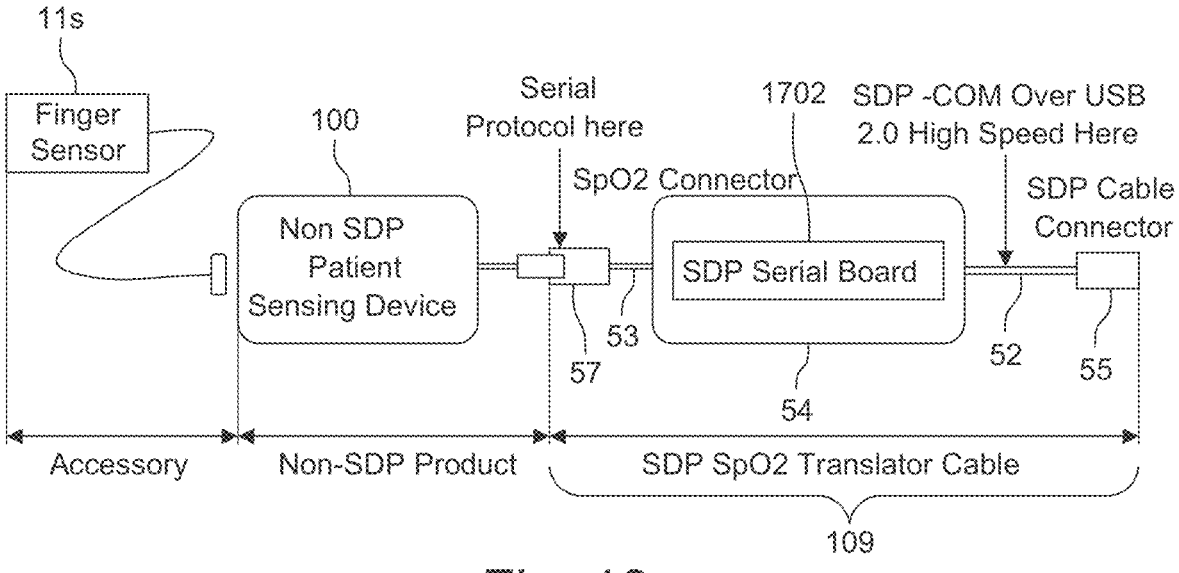
FIG. 19 provides a schematic block diagram of a SDP translation cable for the Sp02 patient parameter according to one or more embodiments.
Figure 22:
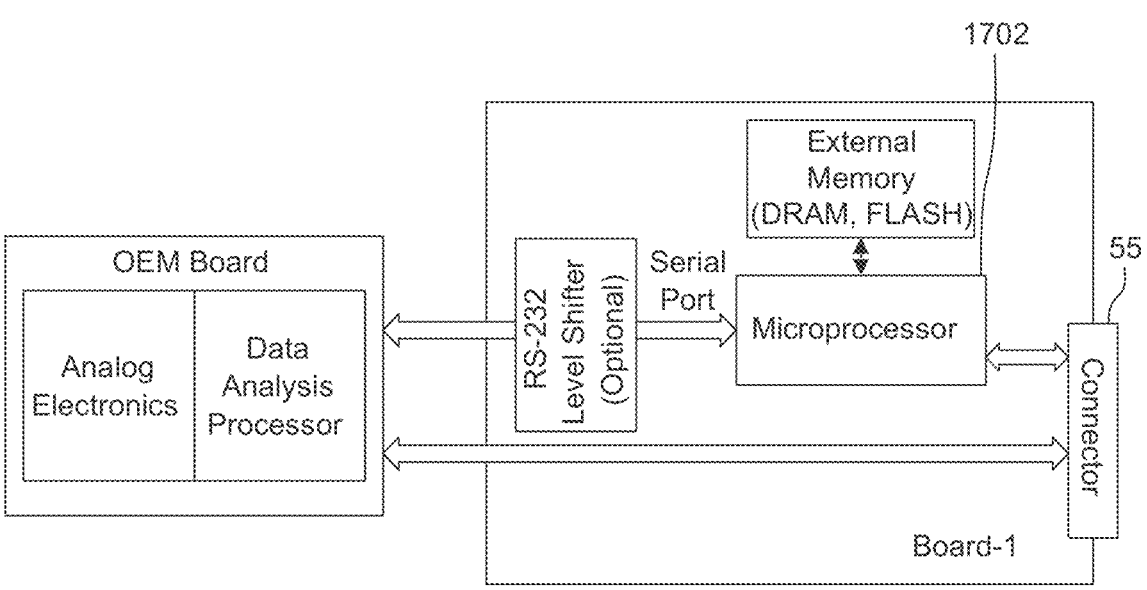
FIGS. 22-25 are schematic diagrams of SDP translation processor boards which are used for non-isolated serial connection to an OEM device, isolated serial connection to an OEM device, isolated serial communication connection for hemodynamic pods that are not self-describing, and a hemodynamic measurement device with isolated pressure and temperature measurements and a serial port for communication with a separate device that performs other measurement functions on the patient, respectively and referenced herein as Board-1, Board-2, Board-3, and Board-4.
Figure 23:
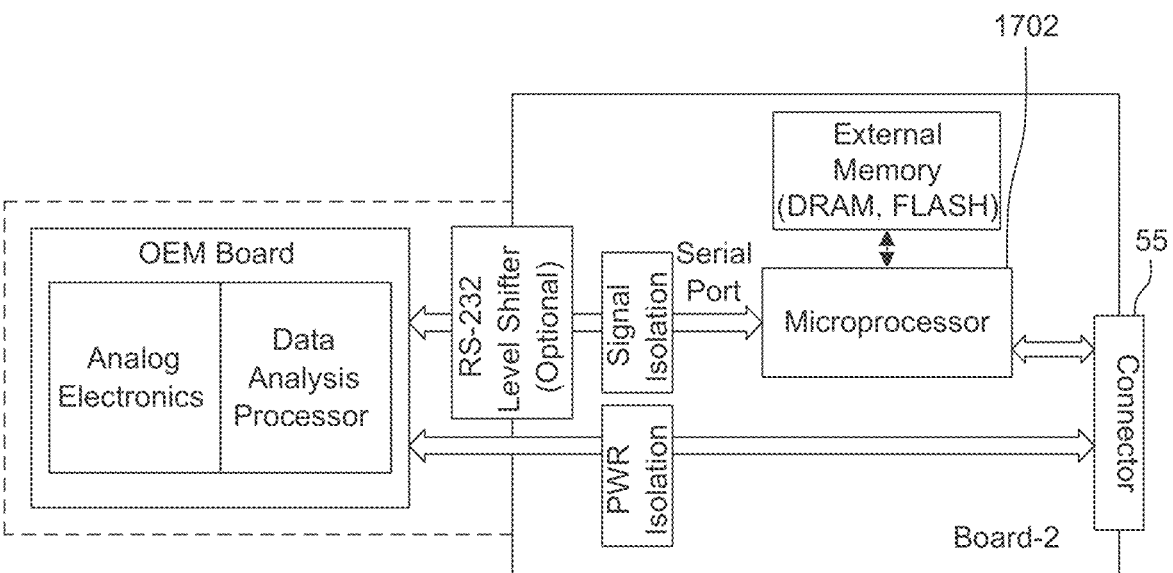

FIG. 19 provides a functional block diagram of a translation device that is used to convert a communication protocol of non-SDP sensor data originating from an Sp02 sensor (i.e., sensor 11s). The Sp02 sensor measures the fraction of hemoglobin in blood that is carrying oxygen. The fraction is stated as a saturation percentage or Sp02. The measurement is made by passing red and infrared light through a tissue of interest. Oxygenated and deoxygenated hemoglobin absorb the red and infrared light differently (that is, hemoglobin changes color when it binds oxygen). The measurement can be made in transmission mode by putting the light source and detectors on opposite sides of a tissue sample (e.g., a finger), or it can be made in reflectance mode wherein light penetrates the tissue and is reflected back out, passing through the tissue sample in both directions.

In these embodiments, the use of existing accessories such as the finger sensors are unaffected by the use of the SDP translation device 109. Referring to FIG. 19, the SDP translation device 109 comprises a microprocessor, such as an SDP serial board 1702, that will be programmed to communicate with one or more system components in a non-SDP patient sensing device 100 an Sp02 sensor to obtain data measurements and change settings, and format these measurements according to the SDP(i.e., a different communication protocol) for the SDP configured medical devices and systems described herein. In those embodiments using an SDP translator cable 109, power to the cable 109 can be switched on or off by the SDP serial board 1702 via a power controller integrated thereon. In certain embodiments, current may also be is limited to a preconfigured amount, for example, to no more than 500 mA.

In certain embodiments, a single SDP translation device will support any type of commercially available Sp02 sensors. However, different Sp02 sensor products may use certain communication speeds, protocols, or other attributes. When in operation, the SDP translation device 109 will cycle power to reset the NSDP sensor device (e.g., an Sp02 sensor) and then attempt to communicate with it using another protocol or another communication speed in order to interact within the NSDP sensor device or devices. The SDP translation device 109 comprises a medical-grade USB cable, one or more connectors, an SDP serial board, an indicator light to show whether or not power is on such as a LED, and an enclosure.

In certain embodiments, the SDP translation device 109 provides electrical isolation for both signals and power, as described above in conjunction with FIG. 7C. The processor itself may not be isolated from the medical device 2. That is, they may be on the same side of the electrical isolation barrier, as shown in FIG. 7C. Patients may be defibrillated when the product is in use, hence the SDP translation device 109 must be defibrillation-proof as a Type F device. Having the processor located on the SDP side of the translation device 109 and thereby electrically isolated from the defibrillator that is connected to the NSDP side of the translation device 109 may protect the processor from surges.

FIGS. 20A and 20B provide illustrations of an SDP translation device configured to be connected with hemodynamic sensor devices.

Referring to FIGS. 20A and 20B, both translation devices consist of the translator electronics, an enclosure 54 or housing that houses an SDP serial communications board, and two cables with molded-on strain-relief features. A red/green LED indicating applied power and connection state will be visible through the enclosure around the SDP serial communications board.

FIG. 21 provides a schematic of a communication link between the non-SDP device 100 and the SDP translation device 109, which includes translation software 1705 and the SDP library 1706. In the embodiment shown, the SDP uses a USB such as USB 2.0 to implement the lower network layers. The USB provides a hub structure, detection of attached devices, and a means of controlling power to each module or device. The USB 2.0 protocol permits transmission at multiple speeds, including high speed (480 Mbps) and full-speed (12 Mbps). The SDP translation device 109 allows non-SDP devices of both speeds to be used.

The microprocessor board 1704 generates an MDB that complies with the SDP. The microprocessor board 1704 does so by converting non-SDP communication data (i.e., sensor data) received from the non-SDP device 100 into the SDP by referring to the SDP library 1706 and applying a selected conversion algorithm.

In one particular embodiment, the SDPSDP translation device 109 comprises a microprocessor board 1702 that has the following configurable features: a 180 MHz processor (2 MB flash memory and 256 KB SRAM); a serial interface (logic level and RS232); a 16 MB SDRAM; a 8 MB Flash; and a high-speed USB 2.0. The software 1705 that runs on the processor 1704 shown in FIG. 21 may perform one or more of the following tasks: translate data from the non-SDP device received in a non-SDP communication into the SDP that can be put into the MDIB, provide logic for alarm conditions, contain user interface preferences such as setting menus and alarm limits, provide algorithms to perform data analysis, and choose text strings from an index. The SDP software library shown comprises a set of tools that enables the microprocessor board 1702 to perform operations on the MDB including constructing the MDB elements and making updates with new data. The functions described in FIG. 21 may vary depending upon the non-SDP or the OEM device used in the system. Because the board that runs the OEM software varies, SDP-COM is not tied to any specific operating system or architecture and is thus independent therefrom—it can interface with any OEM software. The OEM software modules identified in FIG. 21 designate sections of software code that are specific to the particular non-SDP device with which the translation device is communicating.

Figure 24:
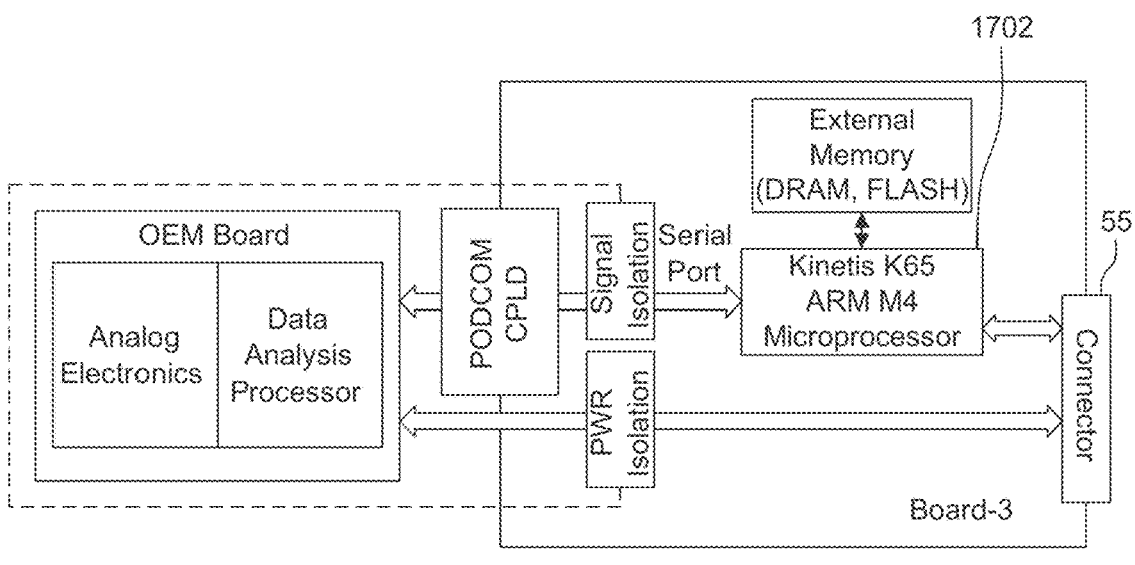
Figure 25:
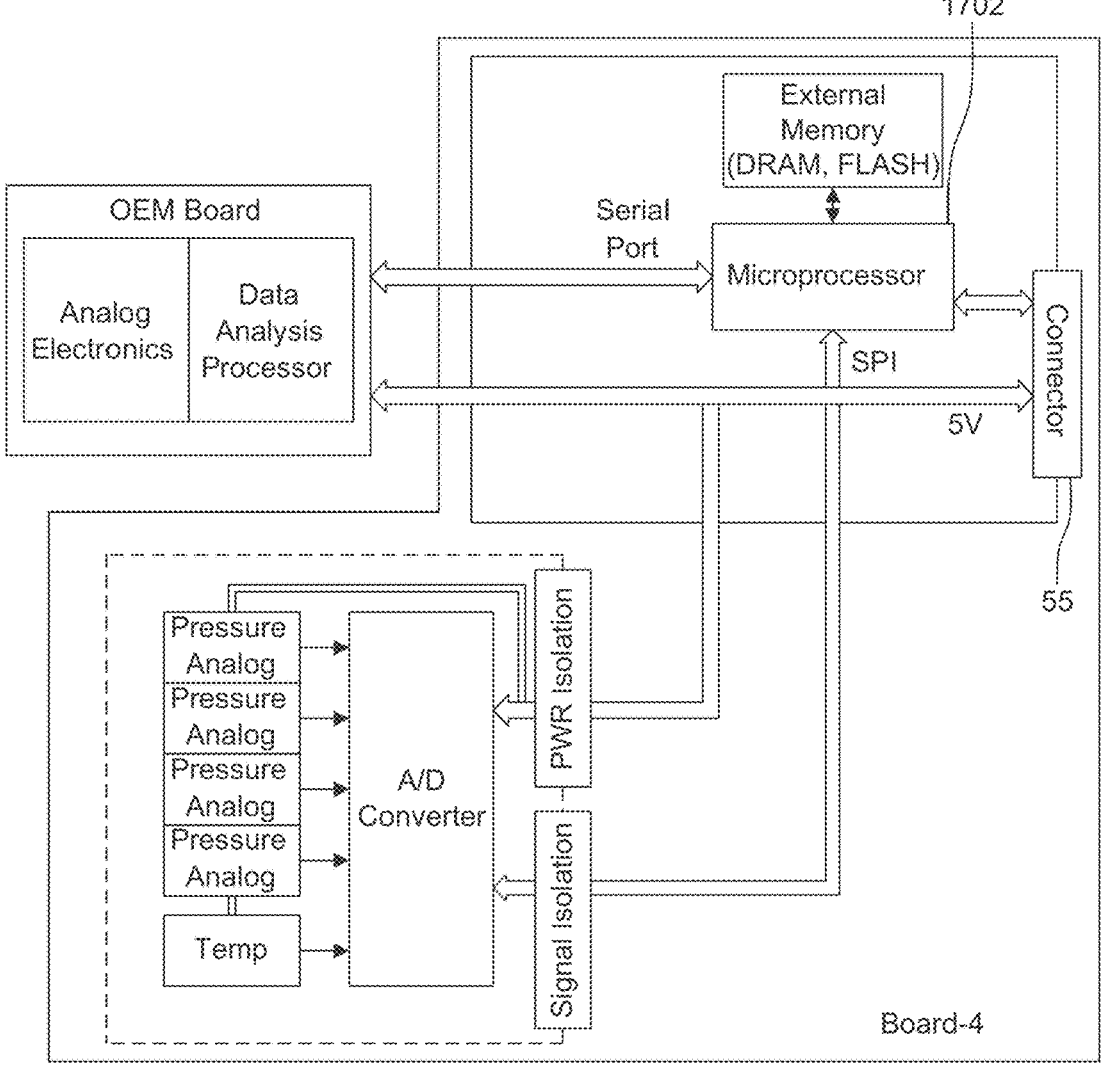

The SDP translation devices described herein may contain any one or more translation processing boards. Examples of embodiments of translation processor boards are shown in FIGS. 22 through 25 (e.g., named as Board-1, Board-2, Board-3 and Board-4). Certain embodiments of processor boards provide basic serial communication, with or without isolation. On either of these boards, the serial output voltage levels can be logic-level (UART) or RS-232. Nearly all of the OEM pods can be made SDP-compatible using any of the foregoing translation processor boards. One particular embodiment of translation processor board is equipped with isolation, as well as an FPGA to implement the SDP. An adapter cable for the legacy, non-native, OEM, or non-SDP speaking devices can also use this translation processor board. Yet another embodiment of a translation processor board may be configured to accept input from four IBP sensors such as that shown in FIG. 25. In this embodiment, the translation processor board may also receive an additional OEM or third party board that provides the sensor device electronics. In FIG. 24. a NSDPCOM complex programmable logic device (CPLD) interfaces between the OEM board and the translation processor board (Board-3).

The pods may share many characteristics as those described in conjunction with FIG. 14. Both will be housed in enclosures that provide space for up to four IBP sensors. Displays over each pressure sensor will indicate the label the user has assigned to the pressure through the monitor user interface. The number of characters per display and the display technology (e.g., LCD, LED, and the like) may be chosen during the detailed design of the pods. Both of the pods will support disposable pressure sensors (200-3000 W, sensitivity of 5 uV/V/mmHg). Both of these pods may be implemented using SDP processor board-4 shown in FIG. 25.

Figure 26A:
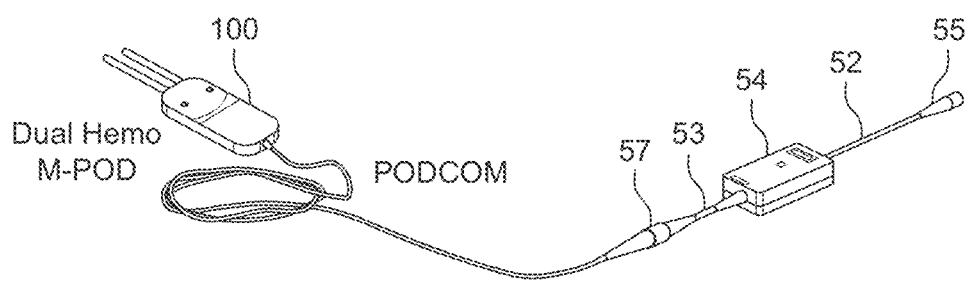
FIGS. 26A and 26B provides schematic block diagrams of an SDP translation device, which may be an SDP translator cable, for hemodynamic sensor devices.
Figure 26B:
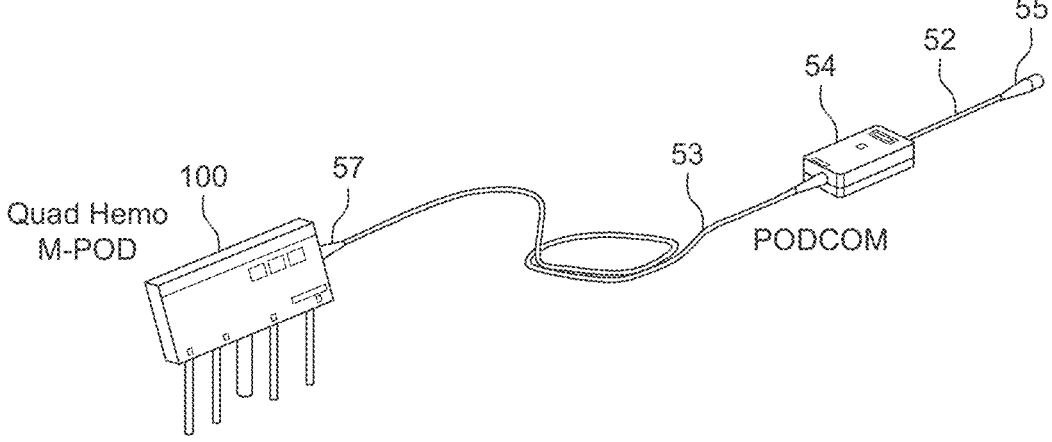

The SDP Hemo translator cable allows users to connect to an SDP port which are shown in FIGS. 26A and 26B for hemodynamic sensor devices, respectively.

FIGS. 26A and 26B shows how these two pods 100 connect to the hemo translator cables. The hemodynamic sensor device shown in FIG. 26A can be plugged into the medical device 2 using an existing connector 55. This connector 55 will be installed on the end of the cable 52 emanating from the hemo translation cable. Use of existing accessories (pressure sensors, cardiac output) is unaffected by the use of the SDP translation device.

The SDP translation device will contain a microprocessor that will be programmed to communicate with the non-SDP patient sensor device 100 described herein to obtain measurements and change settings, and format these measurements according to the SDP for the medical device 2. The SDP concept takes functions such as alarm detection, provision of text strings in the local language, and data unit conversion (traditionally performed inside a monitor) out of the monitor and puts these responsibilities in the SDP device. Because the non-SDP devices were not designed to be self-describing, the SDP translation device 109 must perform these functions.

In one particular embodiment, the translation device comprises a translator cable that provides electrical isolation for signals and power. In this or other embodiments, the translation device will be isolated in accordance to IEC60601-2-49. The processor itself is not isolated from the medical device 2. Signal isolation occurs between the FPGA and NSDPCOM Transceiver. Isolation of 6400 VDC is provided in this example for the signals and the power pin on the NSDPCOM connector.

SDP communications uses USB 2.0 to implement the lower network layers. The USB provides a hub structure, detection of attached devices, and a means of controlling power to each SDP communicating device. The USB 2.0 protocol permits transmission at multiple speeds, including high speed (480 Mbps) and full-speed (12 Mbps). SDP permits devices of both speeds to be used. The Hemo Translator cable may use the SDP NSDPCOM design.

Figure 27:
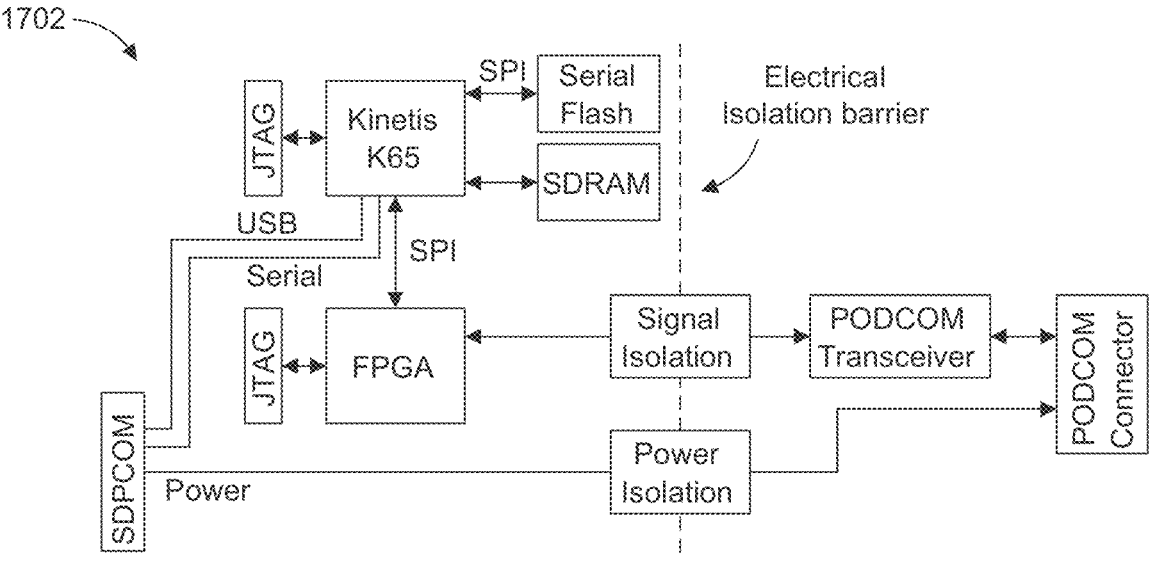
FIG. 27 provides a schematic block diagram of an SDP translation board of an SDP translation device according to one or more embodiments.

FIG. 27 shows a block diagram of another example of an SDP translation board 1702. Like the other SDP translation boards described herein, the NSDPCOM or serial communication design has the following configurable features: a 180 MHz processor (2 MB flash, 256 KB SRAM); a serial interface (logic level and RS232) at up to 115 kbps; 16 MB SDRAM; 8 MB Flash; and Highspeed USB 2.0. Of course, these features are non-limiting and are entirely configurable based on design choice.

As used herein, NSDPCOM is a synchronous bi-directional serial interface used between the NSDP sensor device 100 and the SDP translation device 109 and is used by the SDP translation device 109 to communicate with the NSDP sensor device 100, for example, to obtain physiological patient parameters (i.e., NSDP sensor data). This protocol is used with the hemodynamic sensor devices. In the SDP translation device, this feature is implemented in an FPGA, but is not limited thereto. A SPI interface between the microprocessor and the FPGA to allow the microcontroller to send and receive on the NSDPCOM communication channel.

High-acuity monitors like the medical device described herein provide cardio-synchronous outputs that can be used to drive an intra-aortic balloon pump or defibrillator. The analog output signal must represent the waveform from the invasive pressure sensor at a relatively low latency e.g., a delay of not more than 25 milliseconds (ms). Depending upon the parameter measured, the SDP communication interface is not designed to guarantee low-latency delivery. Thus, the medical device will provide an additional serial line dedicated to transmitting a single pressure signal from an IBP device to the analog subsystem of the SSPPM, bypassing the SDPSDP.

The SDPSDP translation device may be updated remotely if it is attached to a monitor on a serviceable network. This service function will be implemented in all of the SDP communicating or self-describing devices within the system as described herein.

In certain embodiments, system components and devices should be manufactured from a material sufficient to be appropriately cleaned, disinfected, and sterilized for a hospital environment. System components and devices shall maintain basic safety and essential performance during the expected service life when cleaned with medically-approved cleaning agents.

Figure 28:
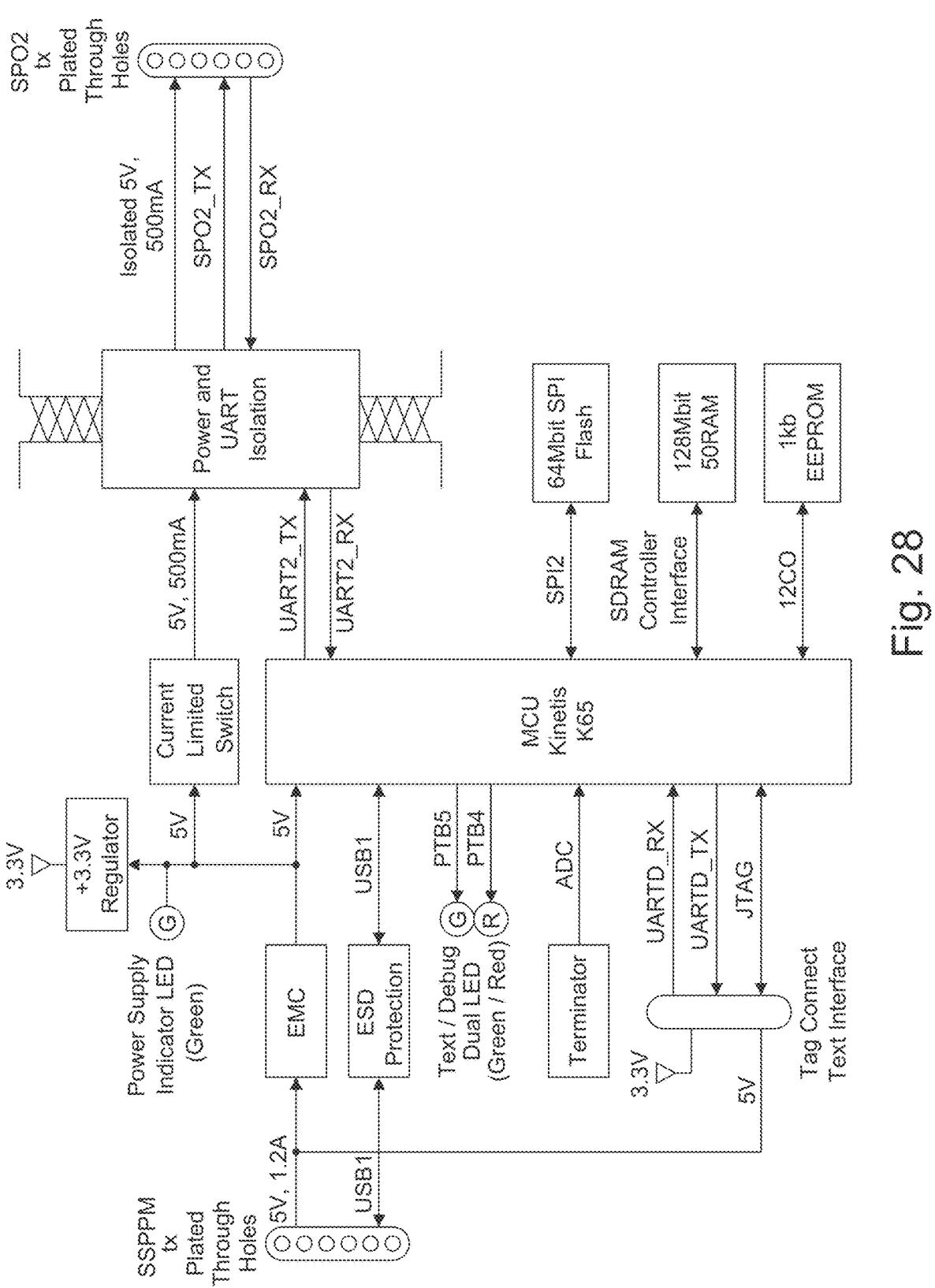
FIG. 28 provides a schematic block diagram of an embodiment of an SDP translation device used with a non-SDP Sp02 device according to one or more embodiments.

FIG. 28 provides an embodiment of a processor board that is used in an SDP translation device such as an SDP translator cable that translates a non-SDP Sp02 sensor data to the SDP communication protocol for communication to a multi-function medical device, such as a patient monitor, therapy device, or medical device. The embodiment depicted comprises, inter alia, a microprocessor board, a thermistor, a power supply indicator light, a 3.3 volt regulator, a current limited switch, a 64 Mbit flash drive, a 120 Mbit SDRAM, an EEPROM, a universal asynchronous receiver-transmitter (UART), and a test/debug dual light emitting diode (LED) light.

Figure 29A:
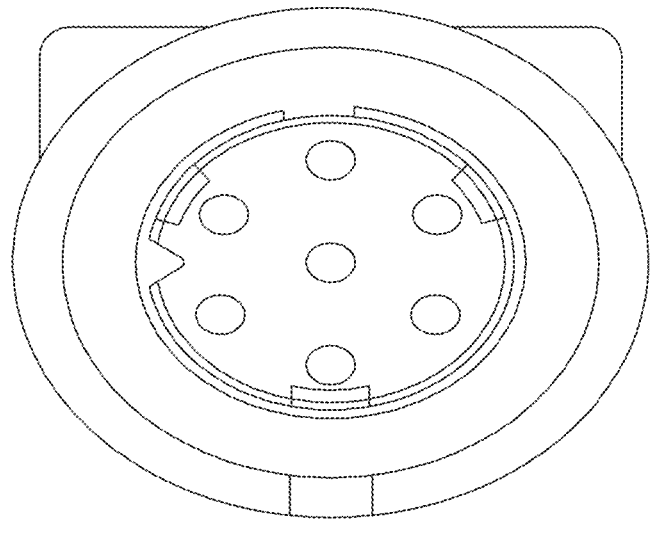
FIGS. 29A-29C provide an embodiment of a female connectors and cable for an SDP translation device comprising a cable according to one or more embodiments.
Figure 29B:
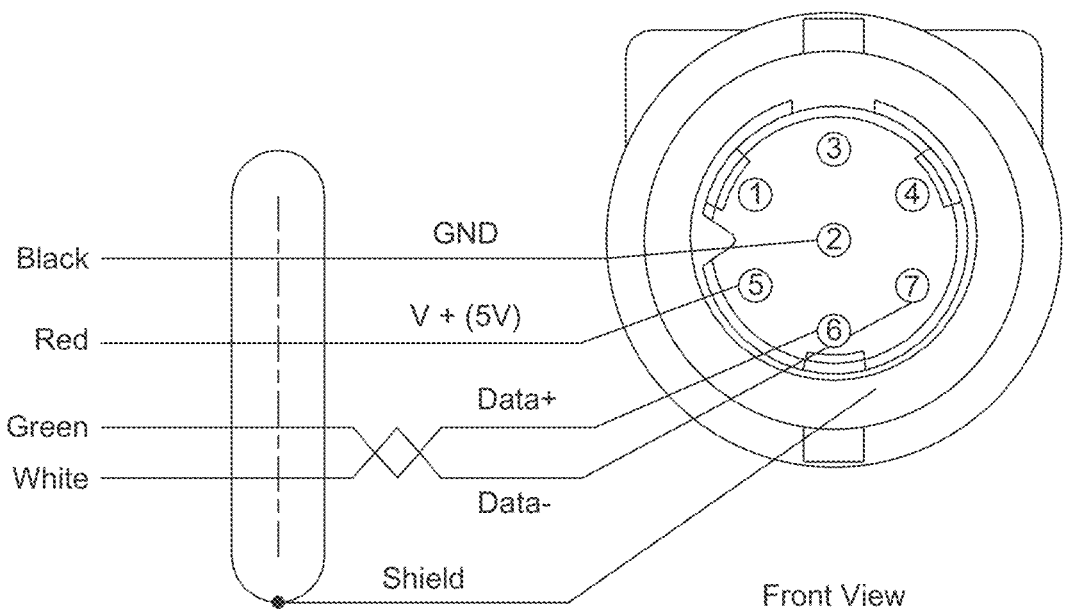
Figure 29C:
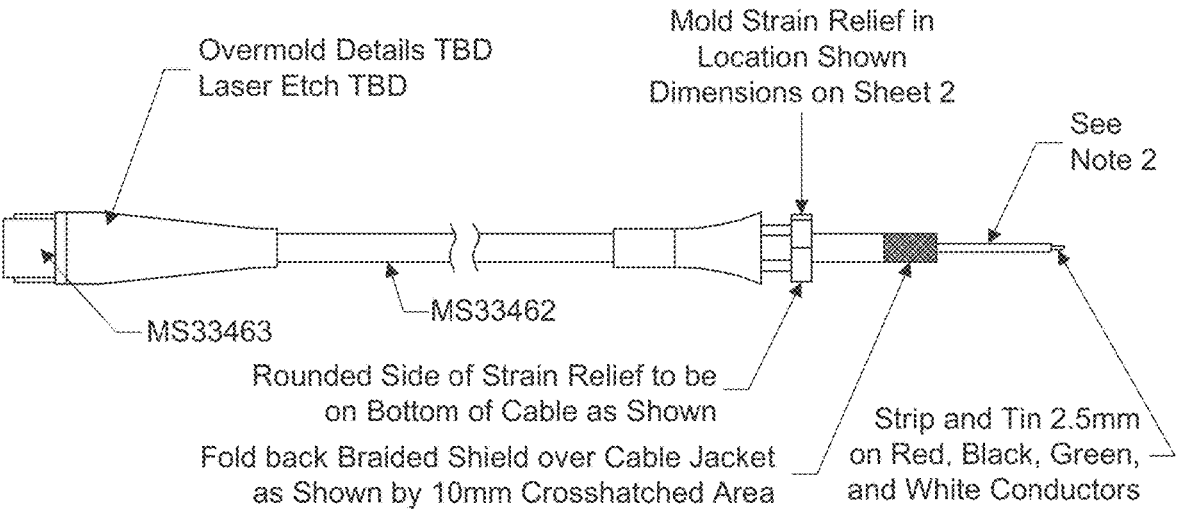

FIGS. 29A-29C provide an example of a cable and multi-pin connector for an SDP translation device, more specifically an SDP translator cable, described herein. FIG. 29B identifies power pins (GND and V+) and data pins. The multi-pin connector may be implemented as connector 55 and/or 57 in the foregoing examples, for example. In addition, the connector may comprise a shield that surrounds the pins of the connector.

Figure 30A:
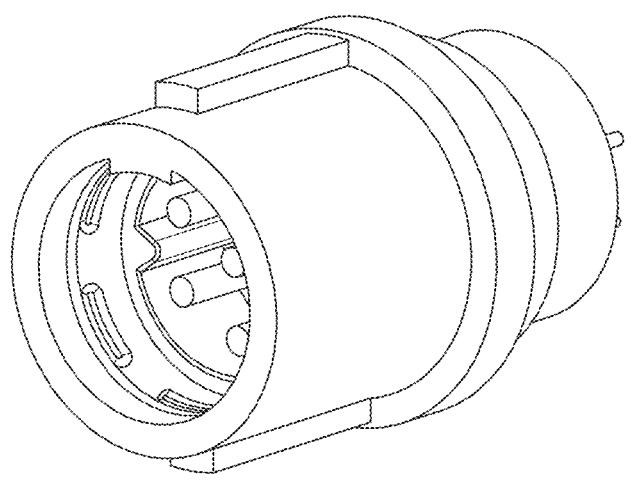
FIGS. 30A and 30B provide an embodiment of a male connector and a female connector for an SDP translation device comprising a cable according to one or more embodiments.
Figure 30B:
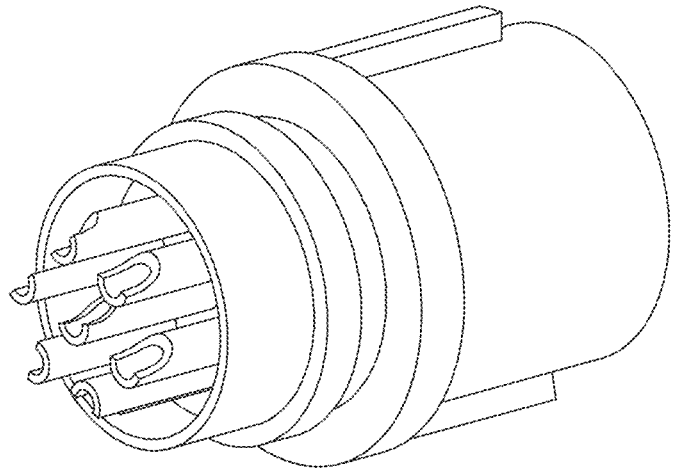

FIGS. 30A and 30B provide an example of a multi-pin male and female connector for an SDP translation device, more specifically an SDP translator cable, described herein.

Figure 31:
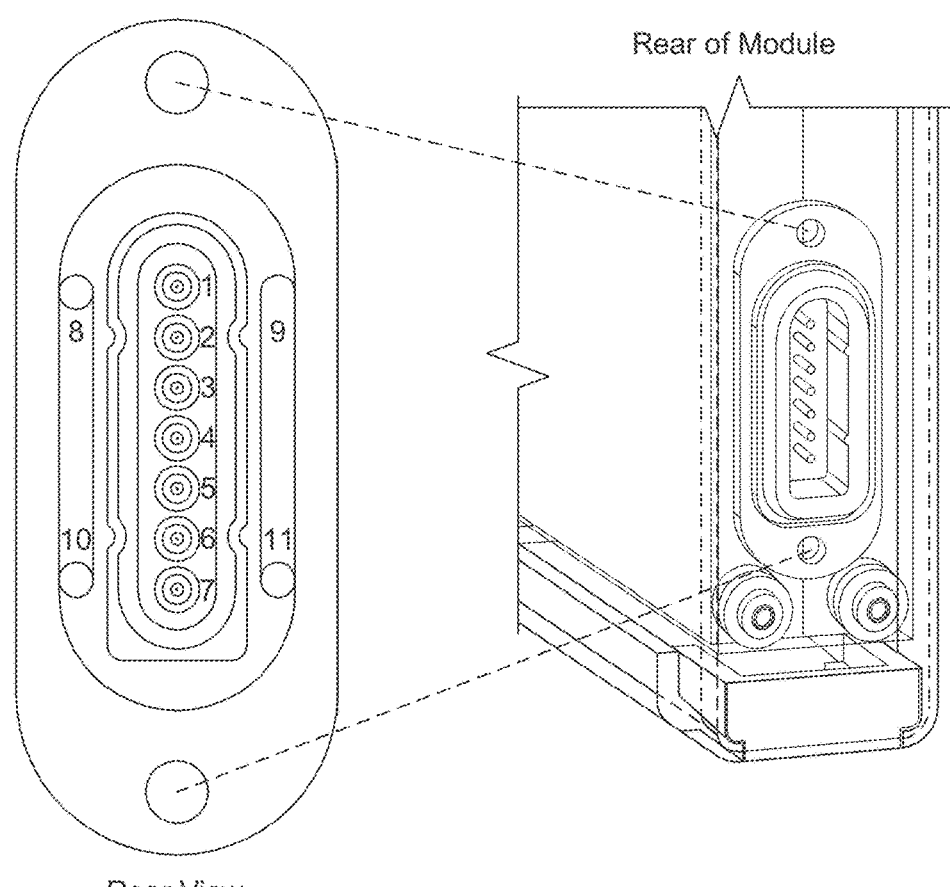
FIG. 31 provides an exemplary module connector and a detailed illustration of the pin connections according to one or more embodiments.

FIG. 31 provides an exemplary module connector and a detailed illustration of the pin connections.

Figure 32:
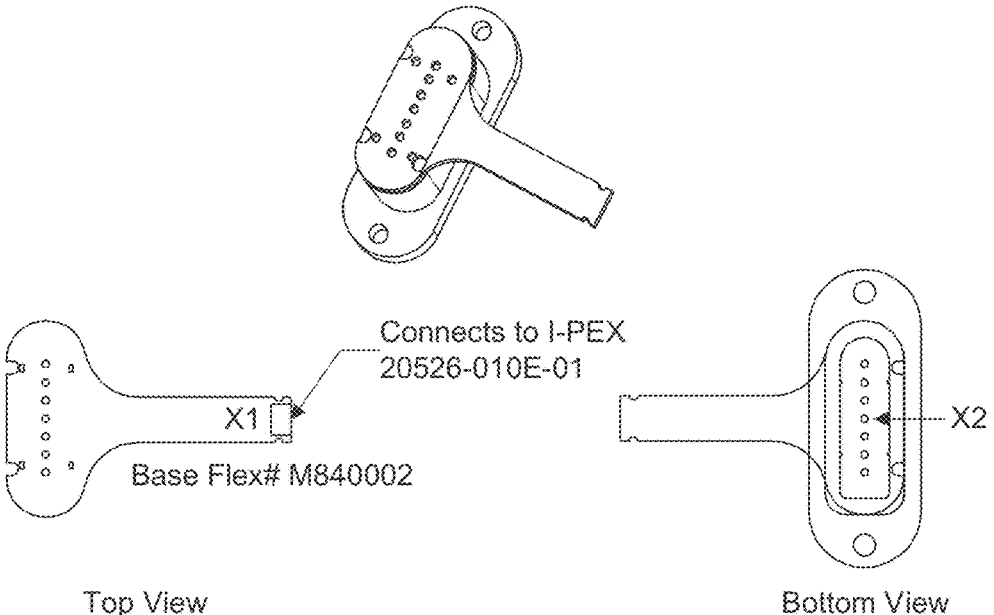
FIG. 32 provides an exemplary flex cable assembly according to one or more embodiments.

FIG. 32 provides an exemplary flex cable assembly.

Figure 33:
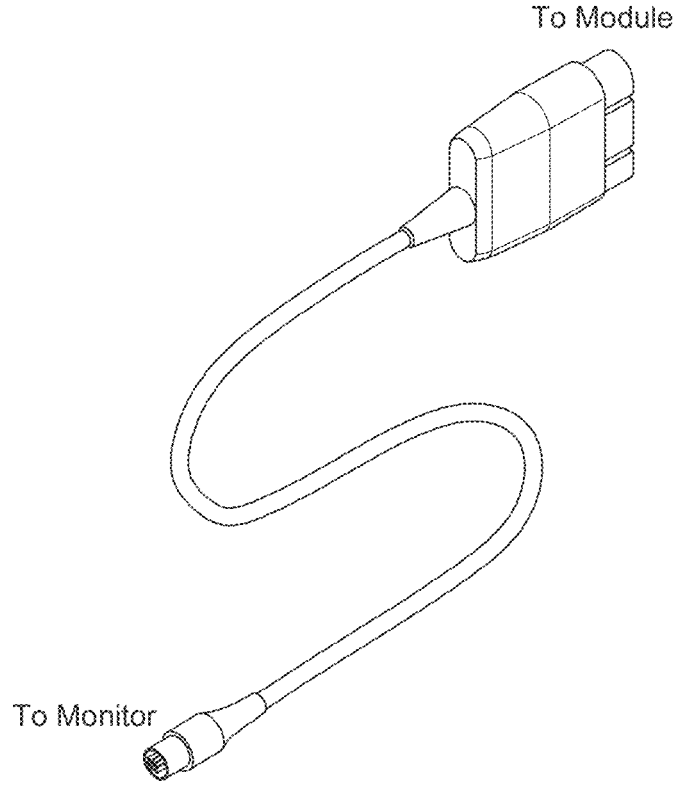
FIG. 33 provides an SDP adapter cable that can be used to allow modules to be connected to system components without a rack according to one or more embodiments.

FIG. 33 provides an exemplary SDP adapter cable that can be used to allow modules to be connected to system components without a rack.

The present disclosure may be implemented as any combination of an apparatus, a system, an integrated circuit, and a computer program on a non-transitory computer readable recording medium. The one more processors may be implemented as an integrated circuit (IC), an application specific integrated circuit (ASIC), or large scale integrated circuit (LSI), system LSI, super LSI, or ultra LSI components which perform a part or all of the functions of the secure conditional access architecture.

The present disclosure includes the use of computer programs or algorithms. The programs or algorithms can be stored on a non-transitory computer-readable medium for causing a computer, such as the one or more processors, to execute the steps described in FIGS. 2-3. For example, the one or more memories stores software or algorithms with executable instructions and the one or more processors can execute a set of instructions of the software or algorithms in association with executing generating, processing provisioning requests and provisioning messages, as described in FIGS. 2-3.

The computer programs, which can also be referred to as programs, software, software applications, applications, components, or code, include machine instructions for a programmable processor, and can be implemented in a high-level procedural language, an object-oriented programming language, a functional programming language, a logical programming language, or an assembly language or machine language. The term computer-readable recording medium refers to any computer program product, apparatus or device, such as a magnetic disk, optical disk, solid-state storage device, memory, and programmable logic devices (PLDs), used to provide machine instructions or data to a programmable data processor, including a computer-readable recording medium that receives machine instructions as a computer-readable signal.

By way of example, a computer-readable medium can comprise DRAM, RAM, ROM, EEPROM, CD-ROM or other optical disk storage, magnetic disk storage or other magnetic storage devices, or any other medium that can be used to carry or store desired computer-readable program code in the form of instructions or data structures and that can be accessed by a general-purpose or special-purpose computer, or a general-purpose or special-purpose processor. Disk or disc, as used herein, include compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

Use of the phrases "capable of," "capable to," "operable to," or "configured to" in one or more embodiments, refers to some apparatus, logic, hardware, and/or element designed in such a way to enable use of the apparatus, logic, hardware, and/or element in a specified manner.

The subject matter of the present disclosure is provided as examples of methods and programs for performing the features of the secure conditional access architecture. However, further features or variations are contemplated in addition to the features described above. It is contemplated that the implementation of the components and functions of the present disclosure can be done with any newly arising technology that may replace any of the above implemented technologies.

Additionally, the above description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, features described with respect to certain embodiments may be combined in other embodiments.

Various modifications to the disclosure will be readily apparent to those skilled in the art, and the generic principles defined herein may be applied to other variations without departing from the spirit or scope of the present disclosure. Throughout the present disclosure the terms "example," "examples." or "example" indicate examples or instances and do not imply or require any preference for the noted examples. Thus, the present disclosure is not to be limited to the examples and designs described herein but is to be accorded the widest scope consistent with the principles and novel features disclosed.

What is claimed:

1. A communication protocol translation system for translating between a non-self-describing protocol (NSDP) and a self-describing protocol (SDP), the system comprising:

an NSDP sensor device comprising sensing electronics coupled to at least one sensor, which is attached to a person and is configured to generate electrical signals representative of at least one physiological parameter of the person, and wherein the NSDP sensor device is generating NSDP sensor data according to the NSDP in response to the electrical signals from the at least one sensor;

a multi-function medical device comprising a processor, wherein the processor is programmed to receive SDP data formatted according to the SDP; wherein the SDP is a set of rules for communicating information using data structures, transmission formats, and defined codes such that the multi-function medical device is enabled to retransmit the information without a priori characterization of the SDP data;

an SDP translating device in communication with the NSDP sensor device and the multi-function medical device; and wherein the SDP translating device is programmed to receive the NSDP sensor data, generate the SDP data based on an NSDP-to-SDP conversion algorithm, and transmit the SDP data to the multi-function medical device.

2. The communication protocol translation system of claim 1, wherein the SDP translating device is programmed to translate the NSDP sensor data into SDP sensor data to generate the SDP data.

3. The communication protocol translation system of claim 2, wherein the SDP translating device comprises a memory that stores a catalog of NSDP-to-SDP conversion algorithms, and the SDP translating device is programmed to identify the NSDP of the NSDP sensor data, select the NSDP-to-SDP conversion algorithm from the catalog of NSDP-to-SDP conversion algorithms based on the identified NSDP, and translate the NSDP sensor data into the SDP sensor data using the selected NSDP-to-SDP conversion algorithm.

4. The communication protocol translation system of claim 2, wherein the SDP translating device is programmed to, while translating the NSDP sensor data into the SDP sensor data, test at least one clinically-relevant quantity of the NSDP sensor data against at least one limit and generate additional SDP signaling information on a condition the at least one clinically-relevant quantity is outside of one of the at least one limit.

5. The communication protocol translation system of claim 2, wherein the SDP translating device is programmed to, while translating the NSDP sensor data into the SDP sensor data, convert a first unit of measure of at least one clinically-relevant quantity of the NSDP sensor data into a second unit of measure that is different from the first unit of measure, and wherein the SDP sensor data provides the at least one clinically-relevant quantity conformed according to the second unit of measure.

6. The communication protocol translation system of claim 2, wherein the SDP translating device is programmed to, while translating the NSDP sensor data into the SDP sensor data, generate descriptive text strings provided with the SDP sensor data, wherein the descriptive text strings characterize at least one clinically-relevant quantity of the SDP sensor data in one or more languages.

7. The communication protocol translation system of claim 2, wherein the SDP translating device is programmed to, while translating the NSDP sensor data into the SDP sensor data, make a temporal change to at least one clinically-relevant quantity of the NSDP sensor data.

8. The communication protocol translation system of claim 2, wherein the SDP translating device is programmed to, while translating the NSDP sensor data into the SDP sensor data, enhance a clinical utility of least one clinically-relevant quantity of the NSDP sensor data.

9. The communication protocol translation system of claim 1, wherein the SDP translating device is programmed to, while translating the NSDP sensor data into the SDP sensor data, generate settings information provided with the SDP sensor data, wherein the settings information permits the multi-function medical device to change how at least one clinically-relevant quantity of the SDP sensor data is processed.

10. The communication protocol translation system of claim 1, wherein the SDP translating device comprises a power circuit coupled to power from the multi-function medical device, wherein the power circuit receives power from the multi-function medical device and distributes a portion of the received power to the NSDP sensor device.

11. The communication protocol translation system of claim 10, wherein the SDP translating device further includes:

a first region from which the SDP data is transmitted to the multi-function medical device, wherein the first region is in electrical contact with the multi-function medical device receives power from the multi-function medical device;

a second region in electrical contact with the NSDP sensor device for receiving the NSDP data therefrom and from which the portion of the received power is distributed to the NSDP sensor device; and an isolation barrier that electrically isolates the first region from the second region.

12. The communication protocol translation system of claim 11, wherein the SDP translating device further includes:

a processing circuit programmed to generate the SDP data based on the NSDP sensor data and the NSDP-to-SDP conversion algorithm, wherein the processing circuit is located in the first region.

13. The communication protocol translation system of claim 12, wherein the power circuit is located in the second region and is configured to distributes a further portion of the received power across the isolation barrier to the processing circuit.

14. The communication protocol translation system of claim 1, wherein the at least one physiological parameter of the person includes at least one of blood pressure, cardiac measurements, pulse oximetry, and respiration information.

15. The communication protocol translation system of claim 1, wherein the multi-function medical device only processes a portion of the NSDP sensor data generated by the NSDP sensor device.

16. A method for translating between a non-self-describing protocol (NSDP) and a self-describing protocol (SDP), the method comprising:

attaching at least one sensor is to a person that is programmed to generate electrical signals based on measuring at least one physiological parameter of the person;

receiving electrical signals from at least one sensor;

generating NSDP sensor data according to the NSDP in response to the received electrical signals from the at least one sensor;

receiving SDP data formatted according to the SDP from a multi-function medical device, wherein the SDP is a set of rules for communicating information using data structures, transmission formats, and defined codes such that the multi-function medical device is enabled to retransmit the information without a priori characterization of the SDP data;

translating the NSDP sensor data into SDP data based on an NSDP-to-SDP conversion algorithm; and transmitting the SDP data to the multi-function medical device.

17. The method of claim 16, further comprising programming the SDP translating device to translate the NSDP sensor data into SDP sensor data to generate the SDP data.

18. The method of claim 17, further comprising:

storing a catalog of NSDP-to-SDP conversion algorithms in a memory of the SDP translating device, programming the translating device to identify the NSDP of the NSDP sensor data, selecting the NSDP-to-SDP conversion algorithm from the catalog of NSDP-to-SDP conversion algorithms based on the identified NSDP, and translating the NSDP sensor data into the SDP sensor data using the selected NSDP-to-SDP conversion algorithm.

19. The method of claim 17, further comprising:

programming the SDP translating device to translate the NSDP sensor data into the SDP sensor data, testing at least one clinically-relevant quantity of the NSDP sensor data against at least one limit, and generating additional SDP signaling information on a condition the at least one clinically-relevant quantity is outside of one of the at least one limit.

20. The method of claim 17, further comprising:

programming the SDP translating device is to translate the NSDP sensor data into the SDP sensor data, and converting a first unit of measure of at least one clinically-relevant quantity of the NSDP sensor data into a second unit of measure that is different from the first unit of measure.

* * * * *